US009265572B2

(12) United States Patent
Fuchs et al.

(10) Patent No.: US 9,265,572 B2
(45) Date of Patent: Feb. 23, 2016

(54) METHODS, SYSTEMS, AND COMPUTER READABLE MEDIA FOR IMAGE GUIDED ABLATION

(75) Inventors: Henry Fuchs, Chapel Hill, NC (US);
Hua Yang, Chapel Hill, NC (US);
Tabitha Peck, Chapel Hill, NC (US);
Anna Bulysheva, Richmond, VA (US);
Andrei State, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 397 days.

(21) Appl. No.: 12/842,261

(22) Filed: Jul. 23, 2010

(65) Prior Publication Data
US 2011/0046483 A1    Feb. 24, 2011

Related U.S. Application Data

(63) Continuation of application No. PCT/US2009/032028, filed on Jan. 26, 2009.

(60) Provisional application No. 61/023,268, filed on Jan. 24, 2008.

(51) Int. Cl.
*A61B 8/00* (2006.01)
*A61B 18/14* (2006.01)
(Continued)

(52) U.S. Cl.
CPC ............... *A61B 18/1477* (2013.01); *A61B 8/00* (2013.01); *A61B 8/4245* (2013.01);
(Continued)

(58) Field of Classification Search
CPC .................................. A61B 8/12; A61N 7/02
USPC ......................................................... 600/439
See application file for complete search history.

(56) References Cited

U.S. PATENT DOCUMENTS 3,556,079 A    1/1971  Omizo
4,058,114 A    11/1977 Soldner
(Continued)

FOREIGN PATENT DOCUMENTS

AU    7656896 A    5/1997
AU    9453898 A    4/1999
(Continued)

OTHER PUBLICATIONS

International Search Report for International Application No. PCT/US2009/032028 (Sep. 9, 2009).
(Continued)

*Primary Examiner* — Tse Chen
*Assistant Examiner* — Hien Nguyen
(74) *Attorney, Agent, or Firm* — Jenkins, Wilson, Taylor & Hunt, P.A.

(57) ABSTRACT

The subject matter described herein includes methods, systems, and computer readable media for image guided ablation. One system for image guided ablation includes an ultrasound transducer for producing a real-time ultrasound image of a target volume and of surrounding tissue. The system further includes an ablation probe for ablating the target volume. The system further includes a display for displaying an image to guide positioning of the ablation probe during ablation of the target volume. The system further includes at least one tracker for tracking position and orientation of the ablation probe during the ablation of the target volume. The system further includes a rendering and display module for receiving a pre-ablation image of the target volume and for displaying a combined image on the display, where the combined image includes a motion tracked, rendered image of the ablation probe and an equally motion tracked real-time ultrasound image registered with the pre-ablation image.

21 Claims, 12 Drawing Sheets

(51) Int. Cl.
  *A61B 3/113* (2006.01)
  *A61B 18/02* (2006.01)
  *A61B 18/18* (2006.01)
  *A61B 19/00* (2006.01)

(52) U.S. Cl.
  CPC .............. *A61B 8/4416* (2013.01); *A61B 8/462* (2013.01); *A61B 3/113* (2013.01); *A61B 8/4263* (2013.01); *A61B 18/0218* (2013.01); *A61B 18/148* (2013.01); *A61B 18/18* (2013.01); *A61B 2019/528* (2013.01); *A61B 2019/5263* (2013.01); *A61B 2019/5297* (2013.01)

(56) References Cited

U.S. PATENT DOCUMENTS

| | | |
|---|---|---|
| RE30,397 E | 9/1980 | King |
| 4,249,539 A | 2/1981 | Vilkomerson et al. |
| 4,294,544 A | 10/1981 | Altschuler et al. |
| 4,390,025 A | 6/1983 | Takemura et al. |
| 4,407,294 A | 10/1983 | Vilkomerso |
| 4,431,006 A | 2/1984 | Trimmer et al. |
| 4,567,896 A | 2/1986 | Barnea et al. |
| 4,583,538 A | 4/1986 | Onik et al. |
| 4,620,546 A | 11/1986 | Aida et al. |
| 4,671,292 A | 6/1987 | Matzuk |
| 4,839,836 A | 6/1989 | Fonsalas |
| 4,862,873 A | 9/1989 | Yajima et al. |
| 4,884,219 A | 11/1989 | Waldren |
| 4,899,756 A | 2/1990 | Sonek |
| 4,911,173 A | 3/1990 | Terwillige |
| 4,945,305 A | 7/1990 | Blood |
| 5,076,279 A | 12/1991 | Arenson et al. |
| 5,078,140 A | 1/1992 | Kwoh |
| 5,078,142 A | 1/1992 | Siczek et al. |
| 5,095,910 A | 3/1992 | Powers |
| 5,109,276 A | 4/1992 | Nudelman et al. |
| 5,158,088 A | 10/1992 | Nelson et al. |
| 5,161,536 A | 11/1992 | Vilkomerson et al. |
| 5,193,120 A | 3/1993 | Gamache et al. |
| 5,209,235 A | 5/1993 | Brisken et al. |
| 5,249,581 A | 10/1993 | Horbal et al. |
| 5,251,127 A | 10/1993 | Raab |
| 5,261,404 A | 11/1993 | Mick et al. |
| 5,265,610 A | 11/1993 | Darrow et al. |
| 5,271,400 A | 12/1993 | Dumoulin et al. |
| 5,307,153 A | 4/1994 | Maruyama et al. |
| 5,309,913 A | 5/1994 | Kormos et al. |
| 5,323,002 A | 6/1994 | Sampsell et al. |
| 5,371,543 A | 12/1994 | Anderson |
| 5,383,454 A | 1/1995 | Bucholz |
| 5,394,875 A | 3/1995 | Lewis et al. |
| 5,411,026 A | 5/1995 | Carol |
| 5,433,198 A | 7/1995 | Desai |
| 5,433,739 A | 7/1995 | Sluijter et al. |
| 5,443,489 A | 8/1995 | Ben-Haim |
| 5,446,798 A | 8/1995 | Morita et al. |
| 5,447,154 A | 9/1995 | Cinquin et al. |
| 5,452,024 A | 9/1995 | Sampsell |
| 5,457,493 A | 10/1995 | Leddy et al. |
| 5,474,073 A | 12/1995 | Schwartz et al. |
| 5,476,096 A | 12/1995 | Olstad et al. |
| 5,483,961 A | 1/1996 | Kelly et al. |
| 5,488,431 A | 1/1996 | Gove et al. |
| 5,489,952 A | 2/1996 | Gove et al. |
| 5,491,510 A | 2/1996 | Gove |
| 5,494,039 A | 2/1996 | Onik et al. |
| 5,503,152 A | 4/1996 | Oakley et al. |
| 5,505,204 A | 4/1996 | Picot et al. |
| 5,515,856 A | 5/1996 | Olstad et al. |
| 5,517,990 A | 5/1996 | Kalfas et al. |
| 5,526,051 A | 6/1996 | Gove et al. |
| 5,526,812 A | 6/1996 | Dumoulin et al. |
| 5,529,070 A | 6/1996 | Augustine et al. |
| 5,531,227 A | 7/1996 | Schneider |
| 5,532,997 A | 7/1996 | Pauli |
| 5,541,723 A | 7/1996 | Tanaka |
| 5,558,091 A | 9/1996 | Acker et al. |
| 5,568,811 A | 10/1996 | Olstad |
| 5,570,135 A | 10/1996 | Gove et al. |
| 5,579,026 A | 11/1996 | Tabata |
| 5,581,271 A | 12/1996 | Kraemer |
| 5,588,948 A | 12/1996 | Takahashi et al. |
| 5,608,468 A | 3/1997 | Gove et al. |
| 5,608,849 A | 3/1997 | King, Jr. |
| 5,611,345 A | 3/1997 | Hibbeln |
| 5,611,353 A | 3/1997 | Dance et al. |
| 5,612,753 A | 3/1997 | Poradish et al. |
| 5,625,408 A | 4/1997 | Matsugu et al. |
| 5,628,327 A | 5/1997 | Unger et al. |
| 5,629,794 A | 5/1997 | Magel et al. |
| 5,630,027 A | 5/1997 | Venkateswar et al. |
| 5,647,361 A | 7/1997 | Damadian |
| 5,647,373 A | 7/1997 | Paltieli |
| 5,660,185 A | 8/1997 | Shmulewitz et al. |
| 5,662,111 A | 9/1997 | Cosman |
| 5,699,444 A | 12/1997 | Palm |
| 5,701,898 A | 12/1997 | Adam et al. |
| 5,701,900 A | 12/1997 | Shehada et al. |
| 5,726,670 A | 3/1998 | Tabata et al. |
| 5,728,044 A | 3/1998 | Shan |
| 5,758,650 A | 6/1998 | Miller et al. |
| 5,766,135 A | 6/1998 | Terwilliger |
| 5,784,098 A | 7/1998 | Shoji et al. |
| 5,792,147 A | 8/1998 | Evans et al. |
| 5,793,701 A | 8/1998 | Wright et al. |
| 5,797,849 A | 8/1998 | Vesely et al. |
| 5,807,395 A | 9/1998 | Mulier et al. |
| 5,810,008 A | 9/1998 | Dekel et al. |
| 5,817,022 A | 10/1998 | Vesely |
| 5,820,554 A | 10/1998 | Davis et al. |
| 5,820,561 A | 10/1998 | Olstad et al. |
| 5,829,439 A | 11/1998 | Yokosawa et al. |
| 5,829,444 A | 11/1998 | Ferre et al. |
| 5,851,183 A | 12/1998 | Bucholz |
| 5,870,136 A | 2/1999 | Fuchs et al. |
| 5,891,034 A | 4/1999 | Bucholz |
| 5,920,395 A | 7/1999 | Schulz |
| 5,961,527 A | 10/1999 | Whitmore, III et al. |
| 5,967,980 A | 10/1999 | Ferre et al. |
| 5,991,085 A | 11/1999 | Rallison et al. |
| 6,016,439 A | 1/2000 | Acker |
| 6,019,724 A | 2/2000 | Gronningsaeter et al. |
| 6,048,312 A | 4/2000 | Ishrak et al. |
| 6,064,749 A | 5/2000 | Hirota et al. |
| 6,091,546 A | 7/2000 | Spitzer |
| 6,095,982 A | 8/2000 | Richards-Kortum et al. |
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,160,666 A | 12/2000 | Rallison et al. |
| 6,167,296 A | 12/2000 | Shahidi |
| 6,181,371 B1 | 1/2001 | Maguire, Jr. |
| RE37,088 E | 3/2001 | Olstad et al. |
| 6,216,029 B1 | 4/2001 | Paltieli |
| 6,241,725 B1 | 6/2001 | Cosman |
| 6,245,017 B1 | 6/2001 | Hashimoto et al. |
| 6,246,898 B1 | 6/2001 | Vesely et al. |
| 6,248,101 B1 | 6/2001 | Witmore, III et al. |
| 6,261,234 B1 | 7/2001 | Lin |
| 6,341,016 B1 | 1/2002 | Malione |
| 6,348,058 B1 | 2/2002 | Melken et al. |
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |
| 6,442,417 B1 | 8/2002 | Shahidi et al. |
| 6,447,450 B1 | 9/2002 | Olstad |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |

(56) References Cited

U.S. PATENT DOCUMENTS

| | | |
|---|---|---|
| 6,503,195 B1 | 1/2003 | Keller et al. |
| 6,511,418 B2 | 1/2003 | Shahidi et al. |
| 6,517,485 B2 | 2/2003 | Torp et al. |
| 6,518,939 B1 | 2/2003 | Kikuchi |
| 6,527,443 B1 | 3/2003 | Vilsmeier |
| 6,529,758 B2 | 3/2003 | Shahidi |
| 6,537,217 B1 | 3/2003 | Bjaerum et al. |
| 6,545,706 B1 | 4/2003 | Edwards et al. |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,575,969 B1 * | 6/2003 | Rittman et al. ............... 606/41 |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Olstad et al. |
| 7,110,013 B2 | 9/2006 | Ebersole et al. |
| 7,171,255 B2 * | 1/2007 | Holupka et al. ............... 600/427 |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de la Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,652,259 B2 | 1/2010 | Kimchy et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,797,032 B2 | 9/2010 | Martinelli et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 | 9/2011 | Ikuma et al. |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,167,805 B2 | 5/2012 | Emery et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 8,340,379 B2 | 12/2012 | Razzaque et al. |
| 8,350,902 B2 | 1/2013 | Razzaque et al. |
| 8,482,606 B2 | 7/2013 | Razzaque et al. |
| 8,554,307 B2 | 10/2013 | Razzaque et al. |
| 8,585,598 B2 | 11/2013 | Razzaque et al. |
| 8,641,621 B2 | 2/2014 | Razzaque et al. |
| 8,670,816 B2 | 3/2014 | Green et al. |
| 8,690,776 B2 | 4/2014 | Razzaque et al. |
| 8,831,310 B2 | 9/2014 | Razzaque et al. |
| 2001/0007919 A1 | 7/2001 | Shahidi |
| 2001/0016804 A1 | 8/2001 | Cunningham et al. |
| 2001/0041838 A1 * | 11/2001 | Holupka et al. ............... 600/439 |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |
| 2002/0077540 A1 | 6/2002 | Kienzle, III |
| 2002/0077543 A1 | 6/2002 | Grzeszczuk et al. |
| 2002/0105484 A1 * | 8/2002 | Navab et al. ............... 345/8 |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessman et al. |
| 2002/0198451 A1 | 12/2002 | Carson |
| 2003/0040743 A1 | 2/2003 | Cosman et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |
| 2004/0181144 A1 | 9/2004 | Cinquin et al. |
| 2004/0215071 A1 | 10/2004 | Frank et al. |
| 2004/0238732 A1 * | 12/2004 | State et al. ............... 250/250 |
| 2004/0243146 A1 | 12/2004 | Chesbrough et al. |
| 2004/0243148 A1 | 12/2004 | Wasielewski |
| 2004/0249281 A1 | 12/2004 | Olstad |
| 2004/0249282 A1 | 12/2004 | Olstad |
| 2004/0254454 A1 | 12/2004 | Kockro |
| 2005/0010098 A1 | 1/2005 | Frigstad et al. |
| 2005/0085717 A1 | 4/2005 | Shahidi |
| 2005/0085718 A1 | 4/2005 | Shahidi |
| 2005/0090742 A1 | 4/2005 | Mine et al. |
| 2005/0111733 A1 | 5/2005 | Fors et al. |
| 2005/0159641 A1 | 7/2005 | Kanai |
| 2005/0182316 A1 | 8/2005 | Burdette et al. |

(56) References Cited

U.S. PATENT DOCUMENTS

| | | |
|---|---|---|
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0251148 A1 | 11/2005 | Friedrich |
| 2006/0004275 A1 | 1/2006 | Vija et al. |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0100505 A1 | 5/2006 | Viswanathan |
| 2006/0122495 A1 | 6/2006 | Kienzle, III |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0016035 A1 | 1/2007 | Hashimoto |
| 2007/0032906 A1 | 2/2007 | Sutherland et al. |
| 2007/0073155 A1 | 3/2007 | Park et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kristofferson et al. |
| 2007/0270718 A1 | 11/2007 | Rochetin et al. |
| 2007/0276234 A1 | 11/2007 | Shahidi |
| 2008/0004481 A1 | 1/2008 | Bax et al. |
| 2008/0004516 A1 | 1/2008 | DiSilvestro et al. |
| 2008/0030578 A1 | 2/2008 | Razzaque et al. |
| 2008/0039723 A1 | 2/2008 | Suri et al. |
| 2008/0051910 A1 | 2/2008 | Kammerzell et al. |
| 2008/0091106 A1 | 4/2008 | Kim et al. |
| 2008/0114235 A1 | 5/2008 | Unal et al. |
| 2008/0161824 A1 | 7/2008 | McMillen |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287794 A1* | 11/2008 | Li et al. .................. 600/439 |
| 2008/0287805 A1 | 11/2008 | Li |
| 2008/0287837 A1* | 11/2008 | Makin et al. ............... 601/2 |
| 2009/0024030 A1 | 1/2009 | Lachaine et al. |
| 2009/0118724 A1 | 5/2009 | Zvuloni et al. |
| 2009/0137907 A1 | 5/2009 | Takimoto et al. |
| 2009/0226069 A1 | 9/2009 | Razzaque et al. |
| 2009/0234369 A1 | 9/2009 | Bax et al. |
| 2009/0312629 A1 | 12/2009 | Razzaque et al. |
| 2010/0045783 A1 | 2/2010 | State et al. |
| 2010/0198045 A1 | 8/2010 | Razzaque et al. |
| 2010/0208963 A1 | 8/2010 | Kruecker et al. |
| 2010/0268072 A1 | 10/2010 | Hall et al. |
| 2010/0268085 A1 | 10/2010 | Kruecker et al. |
| 2010/0305448 A1 | 12/2010 | Dagonneau et al. |
| 2010/0312121 A1 | 12/2010 | Guan |
| 2010/0331252 A1 | 12/2010 | Hamrick |
| 2011/0043612 A1 | 2/2011 | Keller et al. |
| 2011/0046483 A1 | 2/2011 | Fuchs et al. |
| 2011/0057930 A1 | 3/2011 | Keller et al. |
| 2011/0082351 A1 | 4/2011 | Razzaque et al. |
| 2011/0130641 A1 | 6/2011 | Razzaque et al. |
| 2011/0137156 A1 | 6/2011 | Razzaque et al. |
| 2011/0201915 A1 | 8/2011 | Gogin et al. |
| 2011/0201976 A1 | 8/2011 | Sanghvi et al. |
| 2011/0230351 A1 | 9/2011 | Fischer et al. |
| 2011/0237947 A1 | 9/2011 | Boctor et al. |
| 2011/0238043 A1 | 9/2011 | Kleven |
| 2011/0251483 A1 | 10/2011 | Razzaque et al. |
| 2011/0274324 A1 | 11/2011 | Clements et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |
| 2012/0035473 A1 | 2/2012 | Sanghvi et al. |
| 2012/0059260 A1 | 3/2012 | Robinson |
| 2012/0071759 A1 | 3/2012 | Hagy et al. |
| 2012/0078094 A1 | 3/2012 | Nishina et al. |
| 2012/0101370 A1 | 4/2012 | Razzaque et al. |
| 2012/0108955 A1 | 5/2012 | Razzaque et al. |
| 2012/0143029 A1 | 6/2012 | Silverstein et al. |
| 2012/0143055 A1 | 6/2012 | Ng et al. |
| 2012/0165679 A1 | 6/2012 | Orome et al. |
| 2012/0259210 A1 | 10/2012 | Harhen et al. |
| 2013/0030286 A1 | 1/2013 | Alouani et al. |
| 2013/0044930 A1 | 2/2013 | Li et al. |
| 2013/0079770 A1 | 3/2013 | Kyle, Jr. et al. |
| 2013/0129175 A1 | 5/2013 | Razzaque et al. |
| 2013/0132374 A1 | 5/2013 | Olstad et al. |
| 2013/0151533 A1 | 6/2013 | Udupa et al. |
| 2013/0178745 A1 | 7/2013 | Kyle, Jr. et al. |
| 2014/0016848 A1 | 1/2014 | Razzaque et al. |
| 2014/0078138 A1 | 3/2014 | Martin et al. |
| 2014/0094687 A1 | 4/2014 | Razzaque |
| 2014/0180074 A1 | 6/2014 | Green et al. |

FOREIGN PATENT DOCUMENTS

| | | |
|---|---|---|
| AU | 1719601 A | 6/2001 |
| AU | 9036301 A | 3/2002 |
| AU | 2003297225 A1 | 7/2004 |
| AU | 2001290363 | 2/2006 |
| BR | 0113882 A | 7/2003 |
| CA | 2420382 C | 4/2011 |
| DE | 60126798 T2 | 10/2007 |
| EP | 0 427 358 A1 | 5/1991 |
| EP | 1955284 | 8/2008 |
| JP | S63-290550 A | 11/1988 |
| JP | H07-116164 A | 5/1995 |
| JP | 2005-058584 | 3/2005 |
| JP | 2005-323669 | 11/2005 |
| JP | 2009-517177 | 4/2009 |
| WO | WO 96/05768 | 2/1996 |
| WO | WO 97/15249 | 5/1997 |
| WO | WO 97/17014 | 5/1997 |
| WO | WO 99/26534 | 6/1999 |
| WO | WO 01/39683 A1 | 6/2001 |
| WO | WO 03/032837 A1 | 4/2003 |
| WO | WO 03/034705 A2 | 4/2003 |
| WO | WO 03/105289 A2 | 12/2003 |
| WO | WO 2005/010711 A2 | 2/2005 |
| WO | WO 2007/019216 A1 | 2/2007 |
| WO | WO 2007/067323 A2 | 6/2007 |
| WO | WO 2007-067323 A3 | 9/2007 |
| WO | WO 2008/017051 A2 | 2/2008 |
| WO | WO 2009/063423 A1 | 5/2009 |
| WO | WO 2009/094646 | 7/2009 |
| WO | WO 2010/057315 A1 | 5/2010 |
| WO | WO 2010-096419 | 8/2010 |
| WO | WO 2011/014687 | 2/2011 |
| WO | WO 2012/169990 A2 | 12/2012 |
| WO | WO 2013/116240 A1 | 8/2013 |

OTHER PUBLICATIONS

"3D Laparoscope," copyright 2007 InnerOptic Technology, Inc. 2 pages.

"Cancer Facts & Figures 2004," www.cancer.org/downloads/STT/CAFF_finalPWSecured.pdf, copyright 2004 American Cancer Society, Inc., printed Sep. 19, 2007, 60 pages.

(56) References Cited

OTHER PUBLICATIONS

"David Laserscanner <-Latest News <-Institute for Robotics and Process Control <-Te . . . ," http://www/rob.cs.tu-bs.de/en/news/david, printed Sep. 19, 2007, 1 page.
"laser scanned 3d model Final" video, still image of video attached, http://www.youtube.com/watch?v+DaLglgmoUf8, copyright 2007 YouTube, LLC, printed Sep. 19, 2007, 2 pages.
"mile robbins—Computer Vision Research—Stereo Depth Perception," http://www.compumike.com/vision/stereodepth. php, copyright 2007 Michael F. Robbins, printed Sep. 19, 2007, 3 pages.
"Olympus Endoscopic Ultrasound System," www.olympusamerica.com/msg_section/download_brochures/135_b_gfum130.pdf, printed Sep. 20, 2007, 20 pages.
"Point Grey Research Inc.—Imaging Products—Triclops SDK Samples," http://www.ptgrey.com/products/triclopsSDK/ samples.asp, copyright 2007 Point Grey Research Inc., printed Sep. 19, 2007, 1 page.
"RUE: Registered Ultrasound-Endoscope," copyright 2007 InnerOptic Technology, Inc., 2 pages.
Advertisement, "Inspeck 3DC 3D Capturor," Inspeck 3DC 3D Capturor (www.inspeck.com), 1998.
Advertisement, "Virtual 3D High Speed Non-Contact Surface Perception," Virtual 3-D Technologies Corporation (www.virtual3dtech.com), Dec. 21, 1998.
Advertisements, "Virtuoso," Visual Interface, Inc. (www.visint.com), Dec. 21, 1998.
Akka, "Automatic Software Control of Display Parameters for Stereoscopic Graphics Images," SPIE vol. 1669: Stereoscopic Displays and Applications III, pp. 31-38 (1992).
Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.
Aylward et al., "Analysis of the Parameter Space of a Metric for Registering 3D Vascular Images," in W. Niessen and M. Viergever (Eds.): MICCAI 2001, LNCS 2208, pp. 932-939, 2001.
Aylward et al., "Intra-Operative 3D Ultrasound Augmentation," Proceedings of the IEEE International Symposium on Biomedical Imaging, Washington, Jul. 2002.
Aylward et al., "Registration and Analysis of Vascular Images," International Journal of Computer Vision 55(2/3), pp. 123-138 (2003).
Azuma et al., "Improving Static and Dynamic Registration in an Optical See-Through HMO," Proceedings of SIGGRAPH '94, Computer Graphics, Annual Conference Series, 1994, 197-204 (1994.
Azuma, "A Survey of Augmented Reality," Presence: Teleoperators and Virtual Environments 6, vol. 4, pp. 1-48 (Aug. 1997).
Badler et al., "Simulating Humans: Computer Graphics, Animation, and Control," Oxford University Press (1993).
Bajura et al., "Merging Virtual Objects with the Real World: Seeing Ultrasound Imagery within the Patient," Computer Graphics, vol. 26, No. 2, pp. 203-210 (Jul. 1992).
Benavides et al., "Multispectral digital colposcopy for in vivo detection of cervical cancer," Optics Express; May 19, 2003; 11(1 0) Optical Society of America; USA.
Beraldin et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, National Research Council of Canada, http://iit-iti.nrc-.
Billinghurst et al.; Research Directions in Handheld AR; Int. J. of Virtual Reality 5(2), 51-58 (2006).
Blais, "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.
Bouguet, "Camera Calibration Toolbox for Matlab," www.vision.caltech.edu/bouguetj/calib_doc, printed Sep. 20, 2007, 5 pages.

Buxton et al.; "Colposcopically directed punch biopsy: a potentially misleading investigation," British Journal of Obstetrics and Gynecology; Dec. 1991; 98:1273-1276.
Cancer Prevention & Early Detection Facts & Figures 2004; National Center for Tobacco-Free Kids; 2004; American Cancer Society; USA.
Cantor et al., "Cost-Effectiveness Analysis of Diagnosis and Management of Cervical Squamous Intraepithelial Lesions," Diagnostic Strategies for SILs; Feb. 1998; 91(2):270-277.
Catalano et al. "Multiphase helical CT findings after percutaneous ablation procedures for hepatocellular carcinoma." Abdom. Imaging, 25(6), 2000, pp. 607-614.
Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1):219-229.
Crawford et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.
Deering, "High Resolution Virtual Reality." Proceedings of SIGGRAPH '92, Computer Graphics, 26(2), 1992, pp. 195-202.
Depiero et al., "3-D Computer Vision Using Structured Light: Design, Calibration and Implementation Issues," The University of Tennessee, pp. 1-46, (1996).
Dodd et al., "Minimally invasive treatment of malignant hepatic tumors: at the threshold of a major breakthrough." Radiographies 20(1),2000, pp. 9-27.
Drascic et al., "Perceptual Issues in Augmented Reality," SPIE vol. 2653: Stereoscopic Displays and Virtual Reality Systems III, pp. 123-134 (Feb. 1996).
Fahey et al., "Meta-analysis of Pap Test Accuracy; American Journal of Epidemiology," 1995 141(7):680-689; The John Hopkins University School of Hvqiene and Public Health; USA.
Final Official Action for U.S. Appl. No. 10/492,582 (Apr. 30, 2009).
Foxlin et al., "An Inertial Head-Orientation Tracker with Automatic Drift Compensation for Use with HMD's," Virtual Reality Software & Technology, Proceedings of the VRST Conference, pp. 159-173, Singapore, Aug. 23-26, 1994.
Fronheiser et al., "Real-Time 3D Color Doppler for Guidance of Vibrating Interventional Devices," IEEE ULTRASONICS Symposium, pp. 149-152 (2004).
Fuchs et al., "Augmented Reality Visualization for Laparoscopic Surgery," Proceedings of Medical Image Computer and Computer-Assisted Intervention, MICCAI '98, pp. 1-10 (1998).
Fuhrmann et al., "Comprehensive calibration and registration procedures for augmented reality," Proc. Eurographics Workshop on Virtual Environments 2001,219-228 (2001).
Garrett et al., "Real-Time Incremental Visualization of Dynamic Ultrasound Volumes Using Parallel BSP Trees,"Proceedings of IEEE Visualization 1996, pp. 235-240, available from www.cs.unc.edu/~andrei/pubs/1996 VIS dualBSP Mac.pdf, printed Sep. 20, 2007, 7 pages.
Georgakoudi et al., "Trimodal spectroscopy for the detection and characterization of cervical precancers in vivo," American Journal of Obstetrics and Gynecology; Mar. 2002; 186(3):374-382; USA.
Herline et al., "Surface Registration for Use in Interactive, Image-Guided Liver Surgery," Computer Aided Surgery 5:11-17 (2000).
Holloway; Registration Error Analysis for Augmented Reality; Presence: Teleoperators and Virtual Environments 6(4), 413-432 (1997).
Hornung et al., "Quantitative near-infrared spectroscopy of cervical dysplasia in vivo," Human Reproduction; 1999; 14(11):2908-2916; European Society of Human Reproduction and Embryology.
Howard et al., An Electronic Device for Needle Placement during Sonographically Guided Percutaneous Intervention, Radiology 2001; 218:905-911.
http://www.planar.com/products/flatpanel_monitors/stereoscopic/ (Printed Dec. 29, 2011).
InnerAim Brochure; 3D Visualization Software for Simpler, Safter, more Precise Aiming, Published no earlier than Apr. 1, 2010.
International Preliminary Report on Patentability for International Application No. PCT/US2009/032028 (Aug. 5, 2010).

(56) References Cited

OTHER PUBLICATIONS

International Search Report and Written Opinion recieved in corresponding PCT Application No. PCT/US2010/024378, mailed Oct. 13, 2010, 9 pages.
InVision System Brochure; A "GPS" for Real-Time 3D Needle Visualization & Guidance, Published no earlier than Mar. 1, 2008.
InVision User Manual; Professional Instructions for Use, Published no earlier than Dec. 1, 2008.
Jacobs et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.
Kanbara et al., "A Stereoscopic Video See-through Augmented Reality System Based on Real-time Vision-Based Registration," Nara Institute of Science and Technology, pp. 1-8 (2000).
Keller et al., "What is it in Head Mounted Displays (HMDs) that really makes them all so terrible!," pp. 1-8 (1998).
Lass, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.
Lee et al, "Modeling Real Objects Using Video See-Through Augmented Reality," Proceedings of the Second International Symposium on Mixed Reality, ISMR 2001, pp. 19-26 (Mar. 14-15, 2001).
Lee et al., "Modeling Real Objects Using Video See-Through Augmented Reality," Presence, vol. 11, No. 2, pp. 144-157 (Apr. 2002).
Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.
Levy et al., An Internet-Connected, Patient Specific, Deformable Brain Atlas Integrated into a Surgical Navigation System, Journal of Digital Imaging, vol. 10, No. 3. Suppl. 1 Aug. 1997: pp. 231-237.
Livingston et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.
Matsunaga et al., "the Effect of the Ratio Difference of Overlapped Areas of Stereoscopic Images on each Eye in a Teleoperation," Stereoscopic Displays and Virtual Reality Systems VII, Proceedings of SPIE, vol. 3957, pp. 236-243 (2000).
Meehan et al., "Effects of Latency on Presence in Stressful Virtual Environment," Proceedings of IEEE Virtual Reality 2003, pp. 141-148, available from http://www.cs.unc.edu/~eve/pubs.html, printed Sep. 20, 2007, 9 pages.
Milgram et al., "Adaptation Effects in Stereo due to Online Changes in Camera Configuration," SPIE vol. 1669-13, Stereoscopic Displays and Applications III, pp. 1-12 (1992).
Mitchell et al., "Colposcopy for the Diagnosis of Squamous Intraepithelial lesions: A metaanalysis," Obstetrics and Gynecology; Apr. 1998; 91(4):626-631.
Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.
Non-Final Official Action for U.S. Appl. No. 12/609,915 (Nov. 9, 2011).
Non-Final Official Action for U.S. Appl. No. 10/492,582 (Aug. 19, 2008).
Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.
Notification of Republication for International Application No. PCT/US2009/032028 (Oct. 19, 2009).
Notification of Transmittal of the International Search Report or the Declaration for International Application No. PCT/US02/33597 (June. 25, 2003).
Ohbuchi et al., "Incremental Volume Reconstruction and Rendering for 3D Ultrasound Imaging," Visualization in Biomedical Computing, SPIE Proceedings, pp. 312-323, (Oct. 13, 1992).
Ohbuchi, "Incremental Acquisition and Visualization of 3D Ultrasound Images," Ph.D. Dissertation, UNC-CH Computer Science Technical Report TR95-023, (1993).
PCT, The International Search Report of the International Searching Authority, mailed Sep. 9, 2009, for case PCT/US2009/032028.
PCT, The International Search Report of the International Searching Authority, mailed Mar. 3, 2011, for case PCT/US2010/043760.
Pogue et al., "Analysis of acetic acid-induced whitening of high-grade squamous intraepithelial lesions," Journal of Biomedical Optics; Oct. 2001; 6(4):397-403.
Raij et al., Comparing Interpersonal Interactions with a Virtual Human to Those with a Real Human; IEEE Transactions on Visualization and Computer Graphics 13(3), 443-457 (2007).
Raz et al., "Real-Time Magnetic Resonance Imaging-Guided Focal Laser Therapy in Patients with Low-Risk Prostate Cancer," European Urology 58, pp. 173-177. Mar. 12, 2010.
Restriction and/or Election Requirement for U.S. Appl. No. 10/492,582 (Apr. 3, 2008).
Robinett et al., "A Computational Model for the Stereoscopic Optics of a Head-Mounted Display," SPIE vol. 1457, Stereoscopic Displays and Applications II, pp. 140-160 (1991).
Rolland et al., "Towards Quantifying Depth and Size Perception in 3D Virtual Environments," Presence: Teleoperators and Virtual Environments 4, vol. 1, pp. 1-21 (1995).
Rolland et al., "Towards Quantifying Depth and Size Perception in Virtual Environments," Presence: Teleoperators and Virtual Environments 4, vol. 1, pp. 24-49 (Winter 1995).
Rolland et al., Towards Quantifying Depth and Size Perception in Virtual Environments, Presence: Teleoperators and Virtual Environments, Winter 1995, vol. 4, Issue 1, pp. 24-49.
Rosenthal et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.
Rosenthal et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf.
Splechtna et al., Comprehensive calibration and registration procedures for augmented reality; Proc. Eurographics Workshop on Virtual Environments 2001, 219-228 (2001).
State et al., "Technologies for Augmented-Reality Systems: Realizing Ultrasound-Guided Needle Biopsies," Proceedings of SIGGRAPH '96, pp. 1-8 (Aug. 1996).
State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.
State et al., "Interactive Volume Visualization on a Heterogenous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.
State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4.
State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).
State et al., "Superior Augmented Reality Registration by Integrating Landmark Tracking and Magnetic Tracking," ACM SIGGRAPH Computer Graphics, Proceedings of SIGGRAPH 1996, pp. 429-438, available from www.cs.princeton.edu/courses/archive/fall01/cs597d/papers/state96.pdf, printed Sep. 20, 2007, 10 pages.

(56) References Cited

OTHER PUBLICATIONS

State, "Exact Eye Contact with Virtual Humans," Proc. IEEE International Workshop on Human Computer Interaction 2007, Rio de Janeiro, Brazil, pp. 138-145 (Oct. 20, 2007).
Symons et al., "What are You Looking at? Acuity for Triadic Eye Gaze," J. Gen. Psychology 131(4), pp. 451-469 (2004).
Takacs et al., "The Virtual Human Interface: A Photorealistic Digital Human," IEEE Computer Graphics and Applications 23(5), pp. 38-45 (2003).
Takagi et al., "Development of a Stereo Video See-through HMD for AR Systems," IEEE, pp. 68-77 (2000).
Takayama et al., "Virtual Human with Regard to Physical Contact and Eye Contact," Kishino, F., Kitamura, U., Kato, H., Nagata, N. (eds) Entertainment Computing 2005, LNCS, vol. 3711, pp. 268-278 (2005).
U.S. Appl. No. 11/828,826, filed Jul. 26, 2007.
Ultraguide 1000 System, Ultraguide, www.ultraguideinc.com, 1998.
van Staveren et al., "Light Scattering in Intralipid—10% in the wavelength range of 400-1100 nm," Applied Optics; Nov. 1991; 30(31):4507-4514.
Viola et al., "Alignment by Maxmization of Mutual Information," International Journal of Computer Vision, vol. 24, No. 2, pp. 1-29 (1997).
Viola, Paul A., Alignment by Maximization of Mutual Information, Ph.D. Dissertation, MIT-Artificial Intelligence Laboratory Technical Report No. 1548 (Jun. 1995).
Ware et al., "Dynamic Adjustment of Stereo Display Parameters," IEEE Transactions on Systems, Many and Cybernetics, vol. 28, No. 1, pp. 1-19 (Publication Date Unknown).
Watson et al., "Using Texture Maps to Correct for Optical Distortion in Head-Mounted Displays," Proceedings of the Virtual Reality Annual Symposium '95, IEEE, pp. 1-7 (1995).
Welch, Hybrid Self-Tracker: An Inertial/Optical Hybrid Three-Dimensional Tracking System, University of North Carolina Chapel Hill Department of Computer Science, TR 95-048.
Yinghui et al., "Real-Time Deformation Using Modal Analysis on Graphics Hardware," Graphite 2006, Kuala Lumpur, Malaysia, Nov. 29-Dec. 2, 2006.
Zitnick et al., "Multi-Base Stereo Using Surface Extraction," Visual Interface Inc., (Nov. 24, 1996).
Ohbuchi et al., "An Incremental Volume Rendering Algorithm for Interactive 3D Ultrasound Imaging," UNC-CH Computer Science Technical Report TR91-003 (1991).
Notice of Abandonment for U.S. Appl. No. 12/609,915 (Jan. 3, 2013).
Final Official Action for U.S. Appl. No. 12/609,915 (May 25, 2012).
Caines et al., "Stereotaxic Needle Core Biopsy of Breast Lesions Using a Regular Mammographic Table with an Adaptable Stereotaxic Device," American Journal of Roentgenology, vol. 163, No. 2, pp. 317-321, Downloaded from www.ajrorline.org on Jul. 10, 2013 (Aug. 1994).
Dumoulin et al., "Real-Time Position Monitoring of Invasive Devices Using Magnetic Resonance," Magnetic Resonance in Medicine, vol. 29, Issue 3, pp. 411-415 (Mar. 1993).
Fuchs et al., "Optimizing a Head-Tracked Stereo Display System to Guide Hepatic Tumor Ablation," Departments of Computer Sciences and Radiology and School of Medicine, University of North Carolina at Chapel Hill; InnerOptic Technology, Inc., pp. 1-6 (2008).
Fuchs et al., "Virtual Environments Technology To Aid Needle Biopsies of the Breast," Health Care in the Information Age, Ch. 6, pp. 60-61, Presented in San Diego, Jan. 17-20, 1996, published by IOS Press and Ohmsha (Feb. 1996).
Jolesz et al., "MRI-Guided Laser-Induced Interstitial Thermotherapy: Basic Principles," SPIE Institute on Laser-Induced Interstitial Thermotherapy (L1TT), pp. 1-17 (Jun. 22-23, 1995).
Kadi et al., "Design and Simulation of an Articulated Surgical Arm for Guiding Stereotactic Neurosurgery," SPIE vol. 1708 Applications of Artificial Intelligence X: Machine Vision and Robotics, pp. 1-18, Downloaded from: http://proceedings.spiedigitallibrary.org/ on Jul. 11, 2013 (1992).
Kato et al., "A frameless, armless navigational system for computer-assisted neurosurgery," Journal of Neurosurgery, vol. 74, No. 5, pp. 845-849 (May 1991).
PCT International Search Report and Written Opinion of the International Searching Authority for International Application No. PCT/US07/75122 (Aug. 20, 2008).
PCT International Preliminary Report on Patentability (Chapter 1) for International Application No. PCT/US07/75122 (Mar. 3, 2009).
PCT International Search Report and Written Opinion of the International Searching Authority for International Application No. PCT/US2013/023678 (Jun. 13, 2013).
PCT International Preliminary Report on Patentability (Chapter 1) for International Application No. PCT/US2013/023678 (Aug. 5, 2014).
Screenshots from video produced by the University of North Carolina, produced circa 1992.
State et al., "Contextually Enhanced 3D Visualization fro Multi-Born Tumor Ablation Guidance," Departments of Computer Science and Radiology and School of Medicine, University of North Carolina at Chapel Hill; InnerOptic Technology, Inc., pp. 70-77, (2008).

* cited by examiner

METHODS, SYSTEMS, AND COMPUTER READABLE MEDIA FOR IMAGE GUIDED ABLATION

RELATED APPLICATIONS

This application is a continuation of PCT International Patent Application No. PCT/US2009/032028, filed Jan. 26, 2009, which claims the benefit of U.S. Provisional Patent Application Ser. No. 61/023,268, filed Jan. 24, 2008; the disclosures of each which are incorporated herein by reference in their entireties.

GOVERNMENT INTEREST

This presently disclosed subject matter was made with U.S. Government support under Grant No. 1-R01-CA101186-01A2 awarded by the National Institutes of Health. Thus, the U.S. Government has certain rights in the presently disclosed subject matter.

TECHNICAL FIELD

The subject matter described herein relates to image guided medical treatment systems. More particularly, the subject matter described herein relates to methods, systems, and computer readable media for image guided ablation.

BACKGROUND

Ablation, such as radio frequency ablation (RFA), microwave ablation, and cryo-ablation, is a first-line treatment for non-resectable hepatic and other types of tumors. RFA is a minimally invasive intervention (MII) uses high-frequency electrical current, introduced—under 2D ultrasound guidance—via a percutaneous needle-like probe, to heat the targeted tissues to physiologically destructive levels. RFA probes are characterized by manufacturer-specified ablation zones that are typically spheres or ellipsoids. The interventional radiologist who performs the procedure must place the probe such that the entire tumor as well as a safety boundary of several millimeters thickness are contained within the predicted ablation area. Frequent tumor recurrence on the periphery of the original tumor [1] indicates that probe placement accuracy may be a major cause for the low 5-year survival rates of hepatic carcinoma patients.

It is believed that physicians will more accurately target RFA to hepatic and other tumors using a contextually correct 3D visualization system than with standard 2D ultrasound alone. If proven beneficial, 3D guidance could decrease the high post-RFA tumor recurrence rate [3]. Prior experience in developing and evaluating a guidance system for breast biopsy [5] yield results that support this hypothesis.

Accordingly, there exists a long-felt need for methods, systems, and computer readable media for image guided ablation.

SUMMARY

The subject matter described herein includes methods, systems, and computer readable media for image guided ablation. One system for image guided ablation includes an ultrasound transducer for producing a real-time ultrasound image of a target volume to be ablated and surrounding tissue. The system further includes an ablation probe for ablating the target volume. The system further includes a display for displaying an image to guide position of the ablation probe during ablation of the target volume. The system further includes at least one tracker for tracking position of the ablation probe during the ablation of the target volume. The system further includes a rendering and display module for receiving a pre-ablation image of the target volume and for displaying a combined image on the display, where the combined image includes a motion tracked, rendered image of the ablation probe and the real-time ultrasound image registered with the pre-ablation image of the target volume.

The subject matter described herein for image guided ablation may be implemented using a computer readable medium comprising computer executable instructions that are executed by a computer processor. Exemplary computer readable media suitable for implementing the subject matter described herein includes disk memory devices, programmable logic devices, and application specific integrated circuits. In one implementation, the computer readable medium may include a memory accessible by a processor. The memory may include instructions executable by the processor for implementing any of the methods described herein for image guided ablation. In addition, a computer readable medium that implements the subject matter described herein may be distributed across multiple physical devices and/or computing platforms.

BRIEF DESCRIPTION OF THE DRAWINGS

The subject matter described herein will now be explained with reference to the accompanying drawings of which:

FIGS. 1A and 1B). Right: fish tank VR system shows 3D virtual image above patient (cf.

FIG. 5 is Left: RFA guidance system in use on a woodchuck with liver tumors. The interventional radiologist wears polarized glasses and a large but lightweight head tracker with infrared LEDs. He holds a tracked ultrasound transducer (left hand) and a tracked RFA probe (right hand). The stereoscopic display (a commercial unit consisting of two LCD panels and a half-silvered mirror) is also equipped with an LED tracking panel on the right side. Right: View inside the stereoscopic display shows the transducer, the echography image, and the RFA probe (cf. FIG. 1B). The ablation region (cf. FIG. 2B) is also shown (wireframe sphere). The target volume (tumor) is visible as a partially hollowed out spherical object.

FIG. 6 is a diagram of a rendered image of a target volume and an ultrasound transducer prior to an ablation pass according to an embodiment of the subject matter described herein.

FIG. 7 is a rendered image of a target volume, an ultrasound transducer, an RFA probe, and a predicted treatment volume according to an embodiment of the subject matter described herein.

FIG. 8 is a rendered image of a target volume with the region treated by a prior ablation pass subtracted from the target volume, a predicted treatment volume, and the RFA probe in ultrasound transducers according to an embodiment of the subject matter described herein.

In FIG. 9, the tracked medical instruments (ultrasound transducer and RFA probe are not shown. A tracked hand-held pointer used for eye calibration can be seen.

FIGS. 5 left and 9) and show both eyes' views simultaneously (the stereo mirror reflects the right eye view from the top LCD monitor.

DETAILED DESCRIPTION

The subject matter described herein includes methods, systems, and computer readable media for image guided ablation. The following paragraphs describe how an exemplary implementation of the present subject matter was designed, comparing the two designs introduced in FIG. 3: a see through head mounted display and a fish tank virtual reality display.

1. Choosing a Display System

Figure 1B:
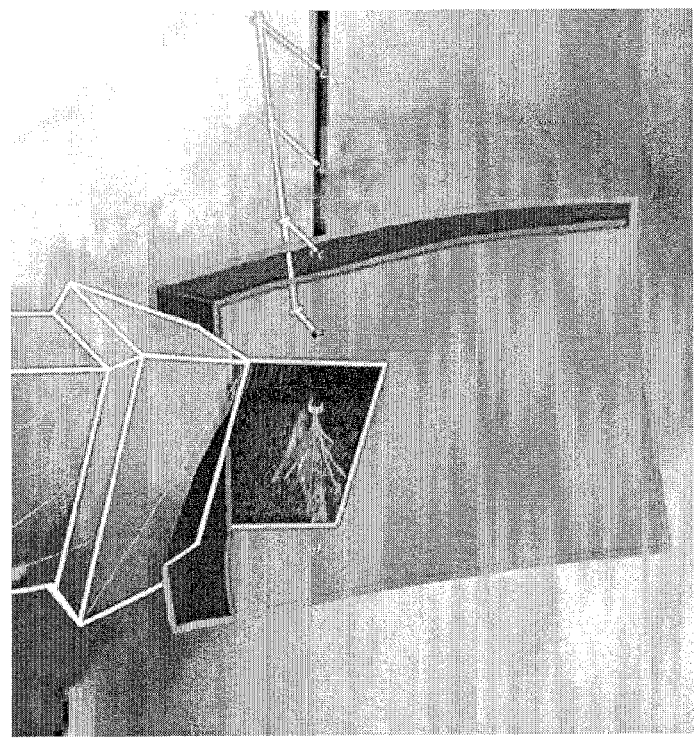
FIG. 1B is a view from inside a head mounted display (HMD) with 3D guidance graphics indicating relationship between needle-like RFA probe and ultrasound image plane.
Figure 2B:
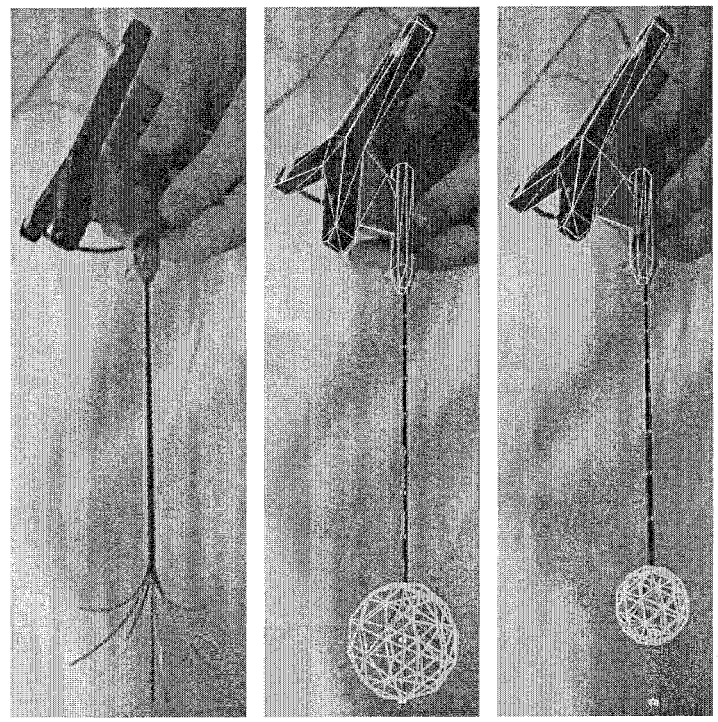
FIG. 2B, from top to bottom, illustrates images of a motion-tracked RFA probe with deployable tines and real-time registered guidance graphics, the ablation region (in this example a sphere) is scaled based on current tine deployment.
Figure 2A:
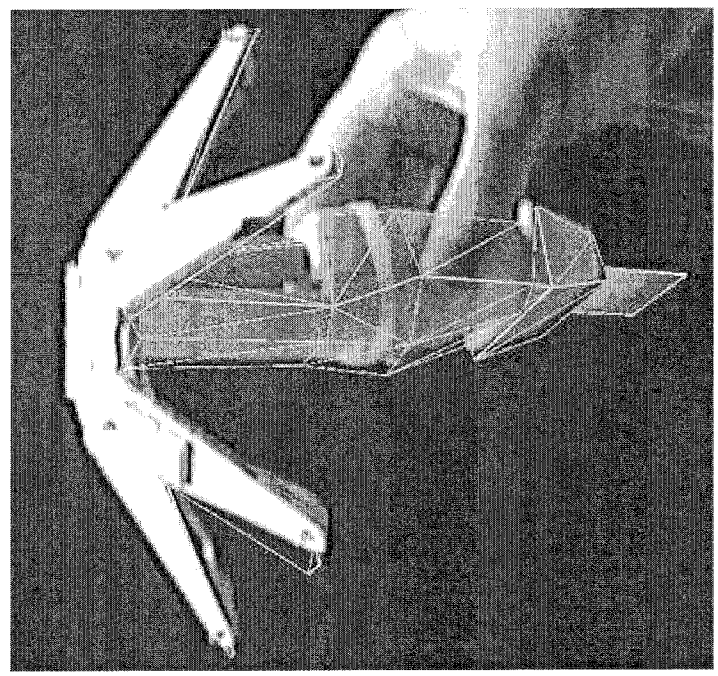
FIG. 2A is a see through head mounted display (ST-HMD) view of an ultrasound transducer with infrared LEDs for motion tracking. The dark rectangle below the transducer is an ultrasound image produced by the ultrasound transducer.

Our research team has developed 3D guidance for MIIs since the mid-1990s; all our systems were based on see-through head-mounted displays (ST-HMDs) [6]. We demonstrated superior targeting accuracy in breast lesions when comparing ST-HMD guidance with the standard 2D method [5]. In addition to stereoscopy and head-motion parallax, the system based on motion-tracked ST-HMDs provided a view of the patient that included a synthetic opening into the patient, showing live echography data and 3D tool guidance graphics in registration with the "real world," and therefore also with the patient (FIG. 1B) as well as with the motion-tracked instruments (note FIG. 2A, which shows the ultrasound transducer in an early RFA guidance system prototype based on a video see-through HMD).

Stereoscopic visualization with head-motion parallax can also be implemented with fixed displays, i.e. without mounting the display on the user's head. Such "fish tank" displays may use CRT monitors and frame-sequential shutter glasses [2], or (at a larger scale) projection displays and passive polarized glasses, for example. Recently, devices based on LCD panels and a semi-transparent mirror have become available from Planar Systems, Inc. [4]; these use passive linearly polarized glasses.

Figure 1A:
FIG. 1A is an image of an RFA guidance system with a see-through head-mounted display.
Figure 3:
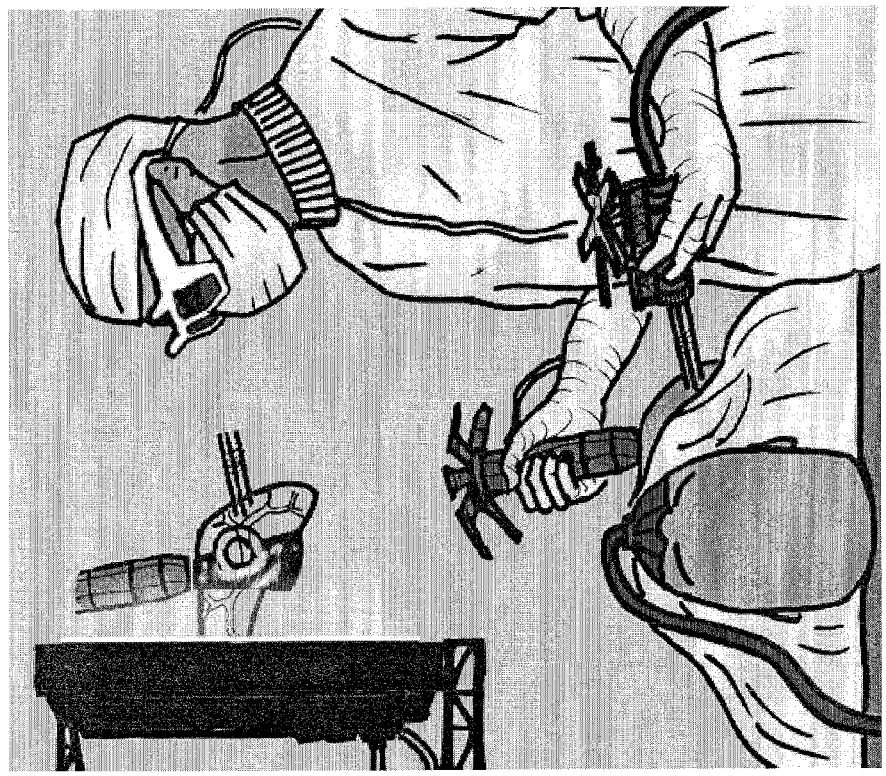
FIG. 3 displays modalities under consideration for the image ablation 3D guidance system, both using optoelectronic tracking (overhead). Left: ST-HMD provides virtual image inside of and registered with the patient (cf.
Figure 3:
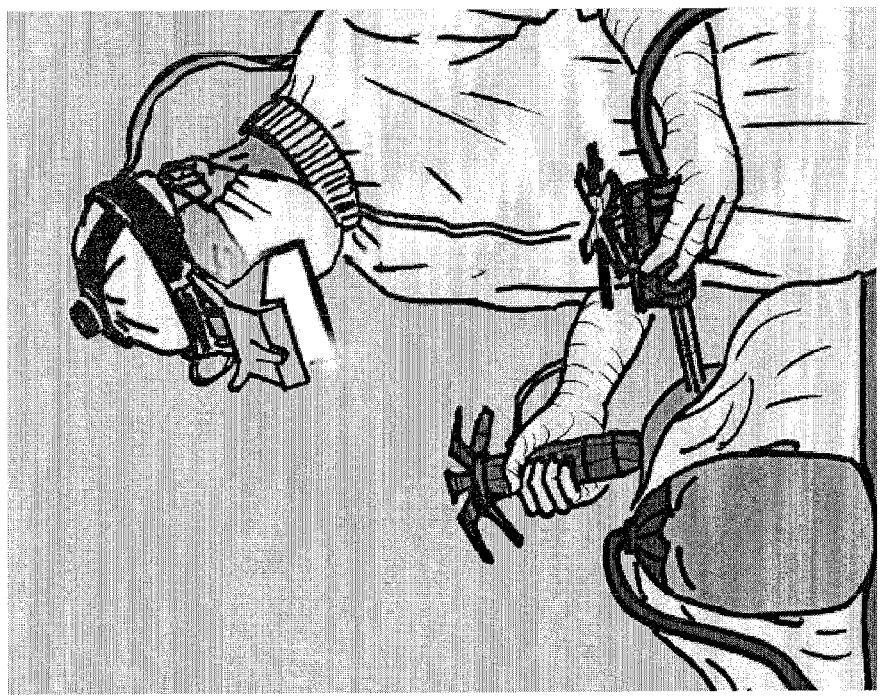

While we obtained encouraging results in the past with ST-HMD systems, we are disappointed with the bulky and uncomfortable, low-resolution devices resulting from today's state of the art in HMDs. Moreover, since there are no satisfactory video see-through devices on the market, we always constructed our own, with rather modest resources [6]. For these reasons, when designing the RFA 3D guidance system, we considered both an ST-HMD approach and a commercial fish tank system (FIG. 3). With respect to the "augmented reality" (AR) view provided by the ST-HMD, we noted that in MIIs—our driving problem—the "interface" between the relevant components of the real world (in our case, the patient, the RFA probe and the ultrasound transducer) and the virtual display (in our case, the echography image, the RFA probe representation inside the patient, and the 3D guidance graphics) is essentially limited to the location where the RFA probe penetrates the skin (FIG. 1A). Furthermore, once the probe pierces the skin, it is moved only lengthwise through this entry point, which is no longer under constant observation by the radiologist. The radiologist then focuses on internal anatomy as he guides the probe into the tumor. From this we conclude that MII (our driving problem) may in fact not derive much benefit from exact registration between real and virtual imagery as provided by an ST-HMD, at least not during the most critical final phase of the probe targeting approach, as the probe tip is introduced into the tumor.

The above considerations led us to favor a fish tank type display even though it does not offer registration between virtual display and internal patient anatomy. Since our display metaphor proposes life-size representations of the ultrasound image and of the ablation probe, projection displays are unsuitable; and CRT-based stereo has disadvantages such as the requirement for active stereo glasses, which can exhibit flicker. The Planar SD1710 display [4] was almost ideally suited: its small 17-inch 1280×1024 display can fully contain our 3D display elements at life size. Furthermore, it does not exhibit flicker and has manageable bulk.

Figure 4:
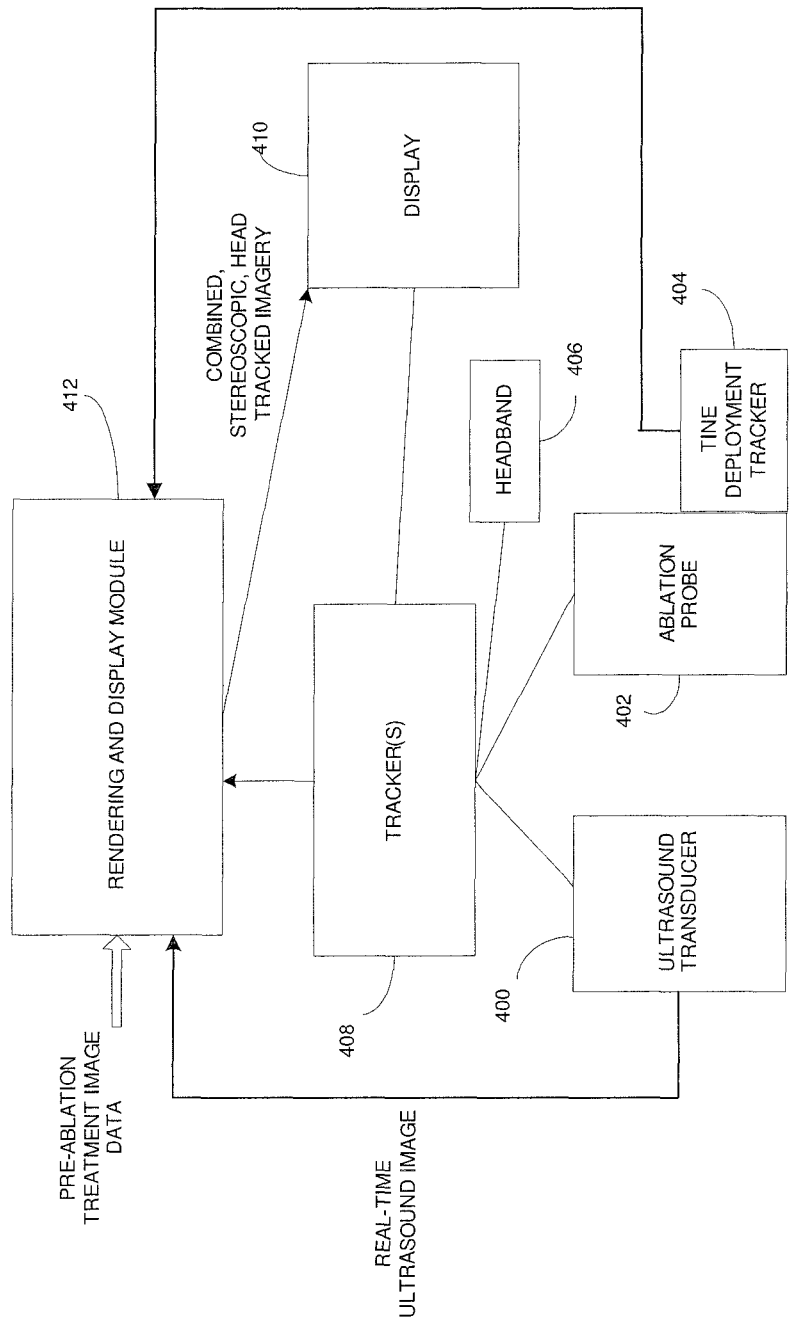
FIG. 4 is a block diagram illustrating an exemplary system for image guided ablation according to an embodiment of the subject matter described herein (this is a fish tank VR system as illustrated in FIG. 3, right).

FIG. 4 is a block diagram illustrating an exemplary system for image guided ablation according to an embodiment of the subject matter described herein. Referring to FIG. 4, the system includes an ultrasound transducer 400 for producing a real-time ultrasound image of a target volume to be ablated and surrounding tissue. Ultrasound transducer 400 may be any suitable ultrasound transducer, such as the type commonly used for surgery, diagnosis, and patient monitoring. Such a transducer produces a real time ultrasound image of the area of the patient near the contact point of the ultrasound transducer with the patient. One disadvantage associated with ultrasound images is that they are usually two-dimensional and they lack the detail of other image types, such as CT and MRI images.

In FIG. 4, the system further includes an ablation probe 402 for ablating the target volume. An exemplary ablation probe suitable for use with embodiments of the subject matter described herein includes the LeVeen RFA needle electrode probe available from Boston Scientific. Probe 402 may also include a tine deployment tracker 404 for tracking deployment of the probe tines (for RFA ablation probes). In one implementation, tine deployment tracker 404 may include a light emitting diode attached to the probe to measure movement of the plunger within the probe that indicates the length of the portions of the tines that are deployed. The LED may be mounted on the plunger and its motion relative the probe handle can be observed by a tracking system. In an alternate embodiment, a linear potentiometer may be used to track tine deployment.

Figure 5:
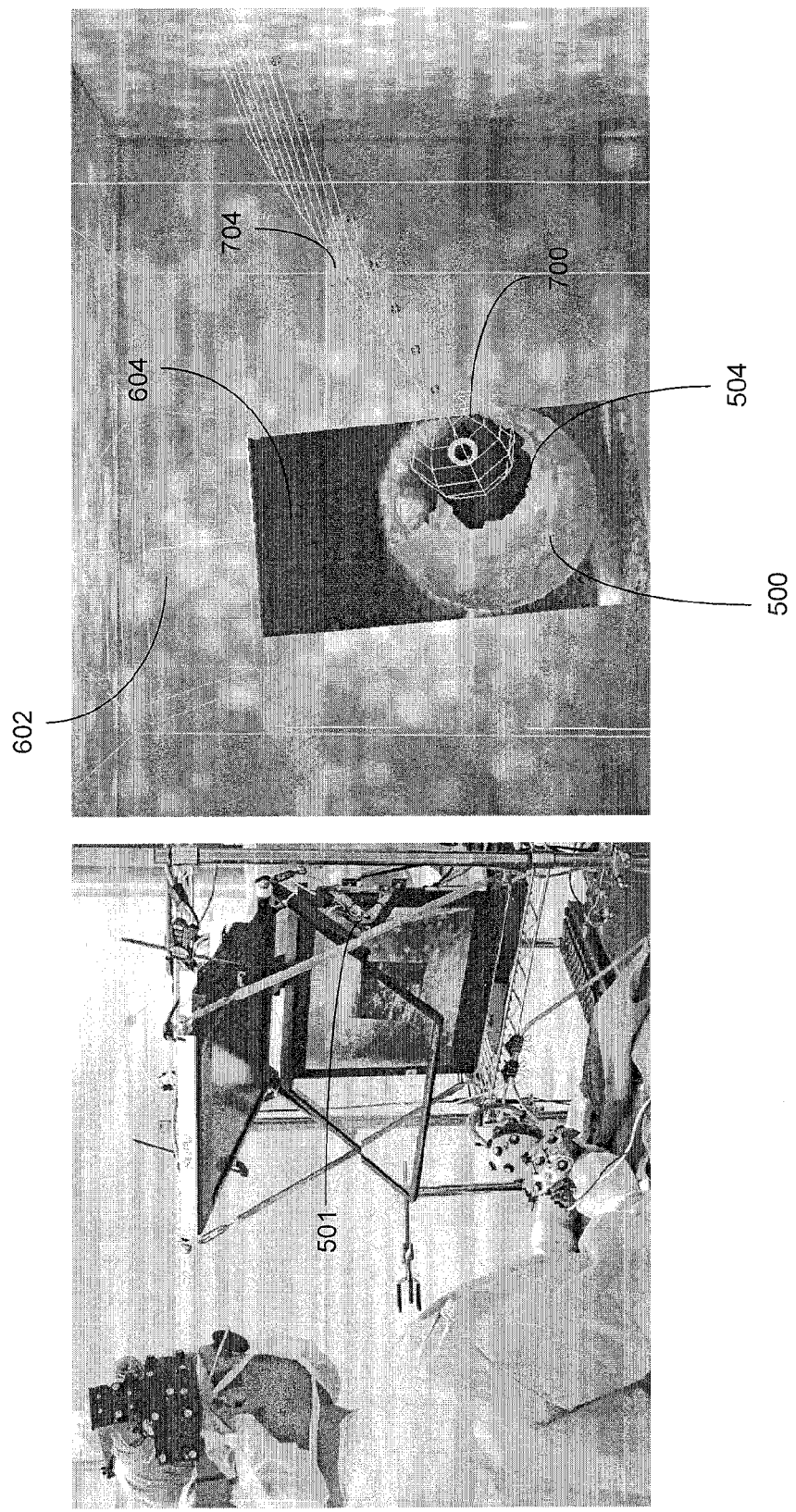
FIGS. 5 through 8).
Figure 9:
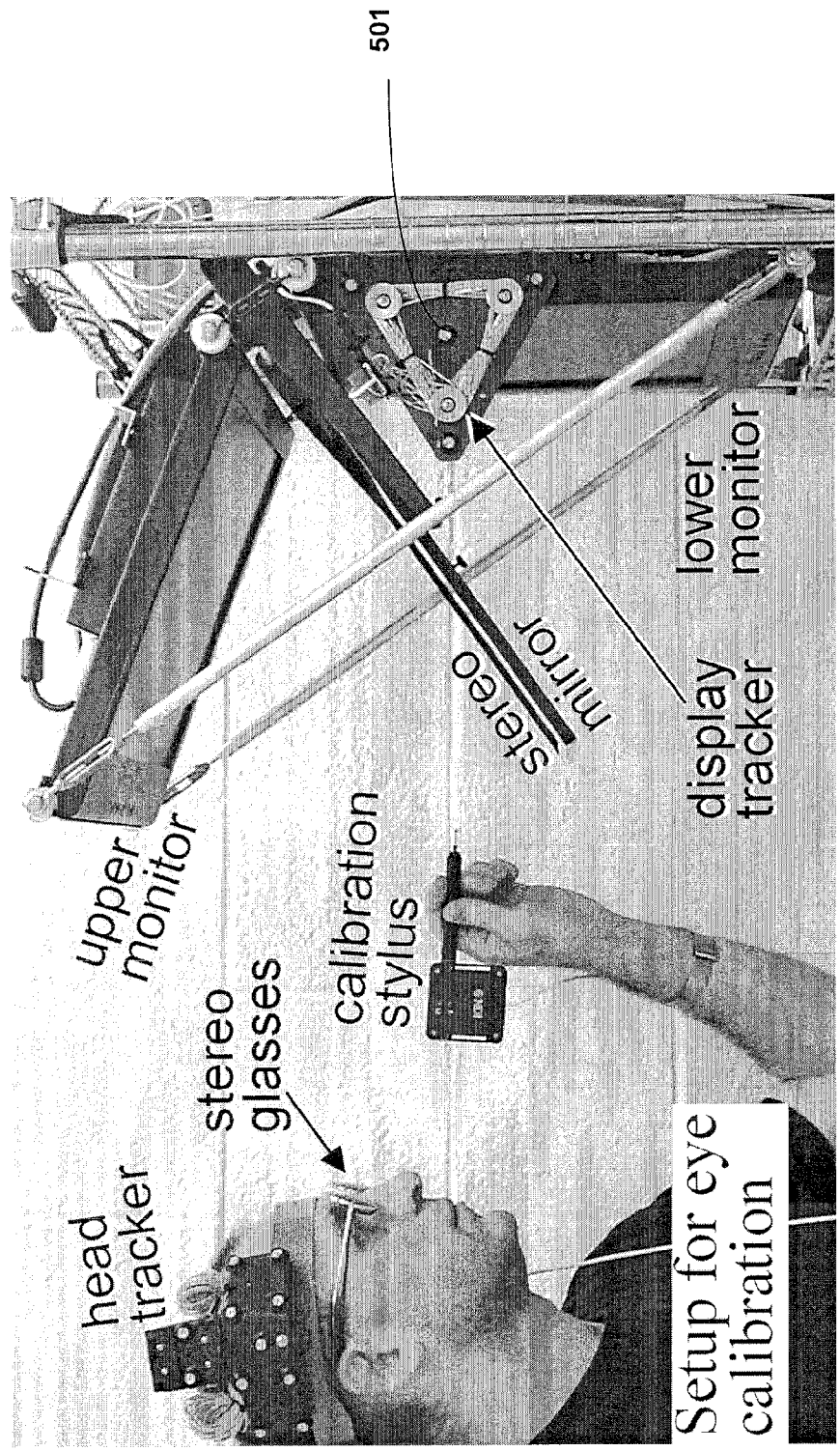
FIG. 9 is a view of a head-tracked virtual environment suitable for use with an image guided ablation guidance system according to an embodiment of the subject matter described herein.

The system illustrated in FIG. 4 further includes a headband 406 to be worn by the user of ablation probe 402. Headband 406 may include a cluster of infrared or other suitable LEDs for tracking purposes. The purpose of headband 406 is to track position and orientation of the user's head to be used in rendering a combined image from the viewpoint of the user onto the stereoscopic fish tank display. A tracker 408 tracks position of the ultrasound transducer 400, ablation probe 402, headband 406, and display 410. Any suitable tracking system for tracking such components can be used. In one implementation, tracker 408 includes a sensor that senses infrared signals from LEDs mounted to ultrasound transducer 400, ablation probe 402, headband 406, and display 410 and computes the positions and orientations of these elements from the signals detected from the LEDs. A triangular LED arrangement 501 suitable for tracking display 410 is shown in FIG. 5 (left) and FIG. 9. Commercially available trackers suitable for use with the subject matter described herein include infrared trackers available from PhaseSpace or Northern Digital, Inc.

The subject described herein is not limited to using a fish tank VR display. As stated above, a virtual see through head mounted display may be used without departing from the scope of the subject matter described herein. In an embodiment that uses a virtual see through head mounted display, tracker 408 can track both the display and the user's head using headband 406, since the display is worn on the user's head.

A rendering and display module 412 receives the real-time ultrasound image, pre-ablation image data, tracking data from tracker 408, produces combined, stereoscopic, head tracked imagery and displays the imagery on display 410. The combined imagery may include a motion tracked, rendered image of the RFA probe, the real-time ultrasound image registered with the pre-ablation image of the target volume, shown from a viewpoint of the user. Exemplary images that may be computed and displayed by rendering and display module 412 will be illustrated and described in detail below.

2. Display System Implementation Details

In one exemplary implementation of the present subject matter, a motion tracker is mounted on the display as in handheld augmented reality applications. Thus, both the tracker base and the stereoscopic display can be moved relative to each other at any time without recalibration to adjust for space and/or line-of-sight constraints within the operating environment; this aims to improve visibility of the tracked system components by the tracker and thereby tracking accuracy and/or reliability. The control software, i.e., rendering and display module 412, ensures that the 3D display preserves orientation; e.g., the virtual representations of tracked devices such as the RFA probe in the display are always shown geometrically parallel to the actual devices, in this case the handheld ablation probe 402. The same applies to the ultrasound transducer 400. In other words, as opposed to the registration in both position and orientation provided by the ST-HMD, this technique maintains only orientation alignment; it introduces a translational offset between the location of the instruments in the real world on the one hand, and their virtual counterparts in the 3D display on the other hand. The interface implemented by rendering and display module 412 has three presentation modes that differ in how these user-induced translational movements of the instruments are echoed in the 3D display (orientation changes are always fully shown, as mentioned):

A. Centered mode: The ultrasound image is always shown in the center of the 3D display. It is not possible to move the ultrasound transducer such that it leaves the display area.

B. Free mode: The user can interactively define the position offset between an area within the patient and the 3D space seen inside the display. Translational motion of the instruments is shown fully within the display, and it is possible to move the ultrasound transducer such that it leaves the display area.

C. Delayed mode: This is a combination of the above two modes. The ultrasound image is initially centered as in (A), but the user may move the ultrasound transducer, even outside the display. However after a short lag, the system "catches up" and re-centers the ultrasound image. This allows the user to perceive high-speed translational motion of the ultrasound transducer and image; at low speeds or statically, this is equivalent to (A), at high speeds, to (B).

For all three modes above, rendering and display module 412 continually calculates the appropriate transformations for the RFA probe, in order to always show the correct pose relationship between it and the ultrasound image.

Given the small size of the display, it is important for the system to accurately track the user's eyes, in order to minimize geometric distortions. A fast and accurate method to calibrate the user's eyes to the head tracker is referenced in the context of which is set forth below [7].

Table 1 summarizes the principal characteristics of the two display techniques we have considered using for the RFA guidance system (ST-HMD and fish tank VR system).

TABLE 1

Characteristics of the two display technologies under consideration

| | See-through HMD | "Fish tank" VR system |
|---|---|---|
| Availability | Custom-designed and built | Commercially available |
| Display configuration | Fixed to user's head, motion-tracked with head | Fixed to room, but motion-tracked (can be moved) |
| Head gear | ST-HMD, tracker | Lightweight glasses, tracker |
| Resolution | 800 × 600 in our recent build; higher resolution yields bulkier device | 1280 × 1024 in current device, available at higher resolutions |
| Registration between patient and ultrasound image (and between RFA probe and its virtual representation) | Yes ("true" augmented reality) | Partial only: orientation alignment but offset in position |

3. Using the Head-Tracked Fish Tank Stereoscopic Display

At present there is no controlled study comparing the performance of the head-tracked fish tank display to an ST-HMD device. An interventional radiologist (Charles Burke, MD, UNC Radiology) who has used the head-tracked fish tank display extensively, reports that depth perception is good and that the display correctly portrays three-dimensional relationships during RFA probe targeting. A depth perception study conducted with this display revealed that most subjects (a randomly selected group of 23) were able to determine which of two objects located only a few millimeters apart in depth was closer, based solely on stereoscopic and motion parallax cues provided by the fish tank display.

The present 3D RF ablation guidance system has been tested on specially constructed liver phantoms; the completed system is currently used in a controlled animal study to ablate liver carcinomas in woodchucks (FIG. 5, left). The study randomizes each woodchuck to either the ultrasound-only conventional guidance method or to the present ultrasound-with-3D-guidance technique.

Figure 6:
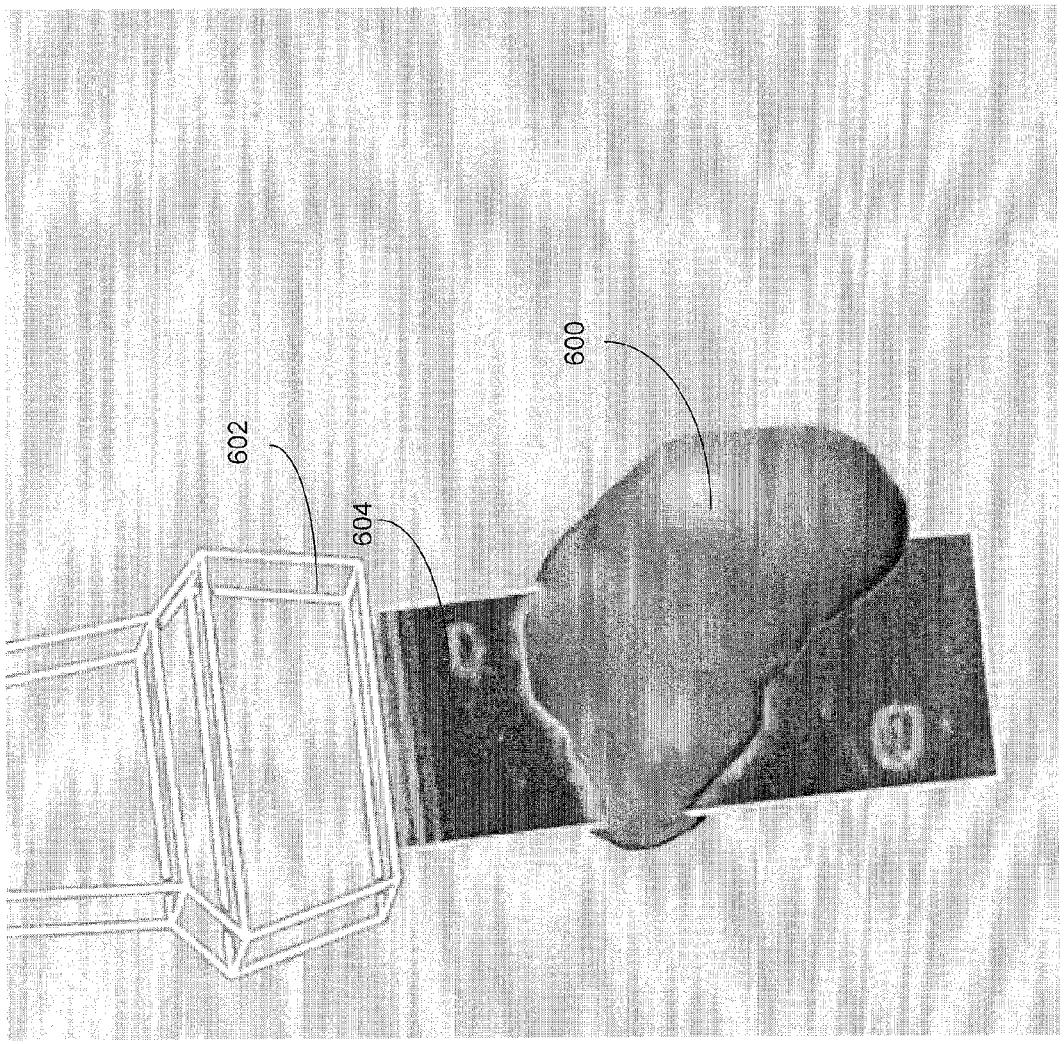

According to one aspect of the subject matter described herein, rendering and display module 412 may display the target volume, such as the tumor, with successively smaller size as ablated regions are eliminated from display with each ablation pass. Such an image is useful for multiple pass techniques that are aim to treat a large tumor with multiple overlapping ablations. In one embodiment, an initial target volume to be ablated may be shown as a three dimensional structure on a display screen. The initial target volume may be rendered from the pre-ablation image data, such as MRI or CT image data. FIG. 6 illustrates an example of an initial target volume that may be displayed by rendering and display module 412. In FIG. 6, three dimensional region 600 represents the initial target volume. Rendering 602 represents ultrasound transducer 400 and its real time orientation. Rendering 604 represents the real time ultrasound image continuously produced by ultrasound transducer 400. Rendering 602 is a virtual representation of ultrasound transducer 400 or, in other words, the ultrasound transducer's avatar.

After a first ablation pass, the volume affected by the first ablation pass may be subtracted from the displayed representation of the initial target volume. The volume affected by the first ablation pass may be determined mathematically based on the position of the ablation probe at the time of the first ablation pass, the geometry of the ablation probe, and the tine deployment and power settings of the ablation probe during the first ablation pass. For example, if the probe is the above-referenced LeVeen needle electrode probe, the affected volume for an ablation pass may be determined based on manufacturers specifications. In one current implementation, a constant ellipsoid based on what the probe data sheet indicates is used as the affected ablation volume may be subtracted from the image of the target volume. In alternate implementations, pre-calibrated volumes (shapes measured in a test ablated human-organ-like phantom) or varying the shape based on time deployment can be used to determine the affected sub volume. However, the probes are usually specified to be used with fully deployed times, and manufacturers do not give partial deployment information. Additional bio-chemo-thermo-geometric calibration and simulation work, possibly taking into account fluid flow through blood vessels, may be utilized to increase the accuracy of the affected ablation volume estimates.

Figure 7:
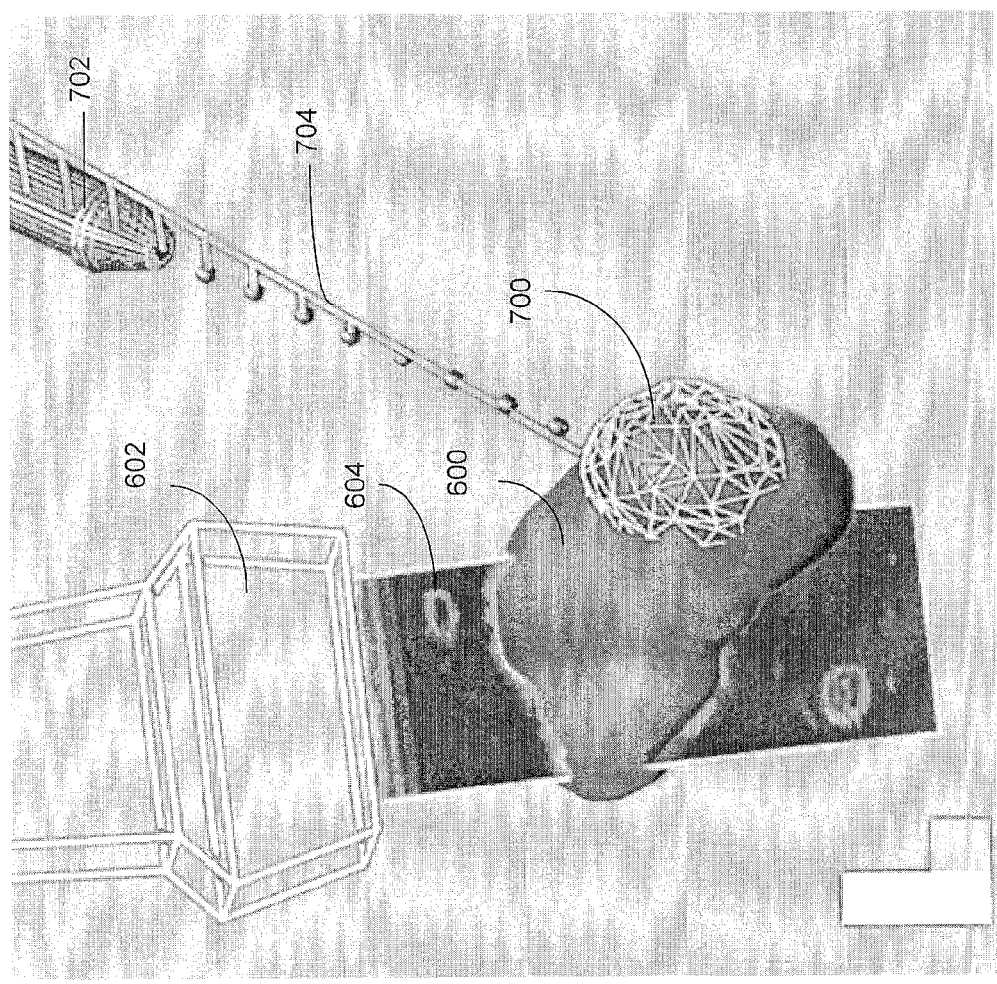
Figure 8:
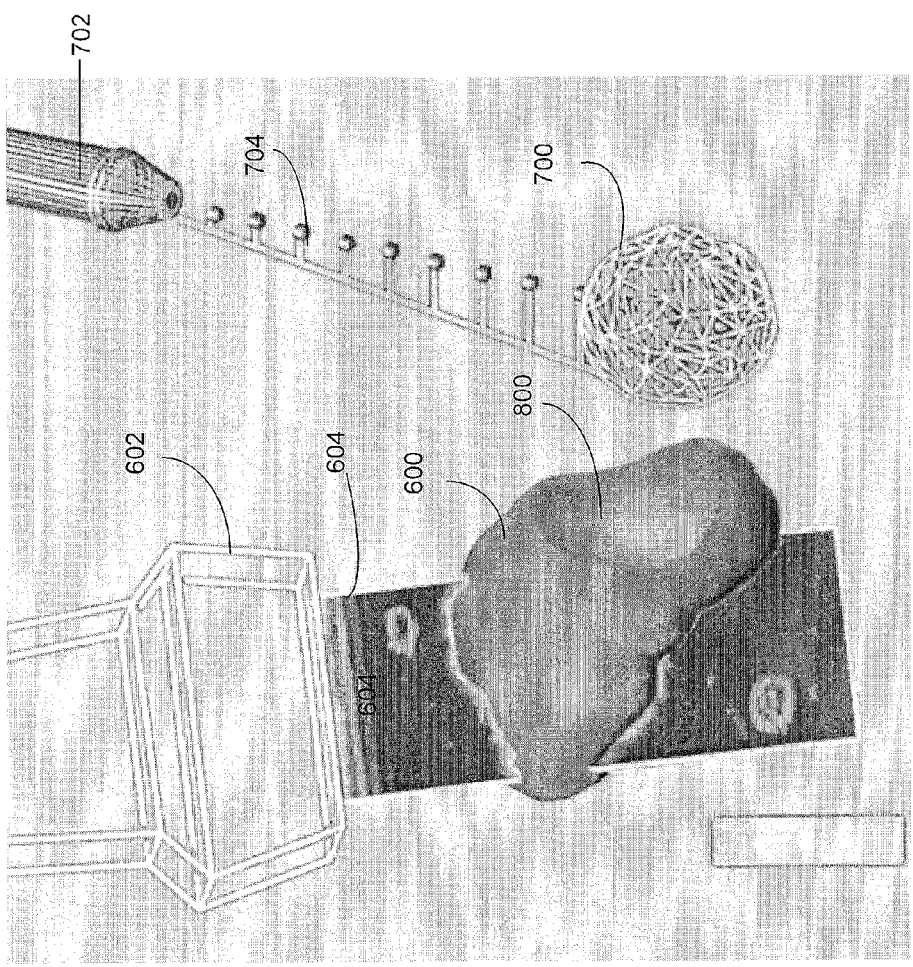

FIG. 7 illustrates initial target volume 600 with the region affected by the first ablation pass shown surrounded by a wireframe region 700 that represents a predicted ablation area. A rendering 702 representing ablation probe 402 and its current orientation is also shown. Rendering 704 represents 3D guidance graphics produced by rendering and display module 412. In the illustrated example, the 3D guidance graphics include a calculated projection of ablation probe 402 onto the plane defined by the current position and orientation of the ultrasound image 604; projection lines connect ablation probe 402's needle to the calculated projection at regular intervals. This is useful in assessing the spatial relationship between ablation probe 402 and the ultrasound image; the probe only appears in the ultrasound image when the two are coplanar, that is, when ablation probe 402's needle coincides with its projection and the projective lines have collapsed to zero length. The predicted ablation area may also be determined based on the current position of the probe, the power settings, tine deployment, and the manufacturer's specification. Once the volume determined by the first ablation pass is determined, that volume can be subtracted and the remaining volume can be displayed to the user in the next ablation pass. FIG. 8 illustrates an example of subtracting the volume affected by the first ablation pass from initial target volume 600 illustrated in FIG. 6. In FIG. 8, concave surface area 800 illustrates the results of subtracting the volume of initial target volume 600 affected by the first ablation pass from the initially displayed target volume. This subtracting can be repeated for successive ablation passes until target volume 600 is eliminated. The display of surfaces 600 and 800 can be formed in real-time using polygon rendering of the isosurface calculated from the affected volume, for example, using the well known marching cubes isosurface extraction technique. As another example of the display of the target volume affected by successive ablation passes, the image on the right-hand side of FIG. 5 is another example of volume carving visualization that may be rendered by rendering and display module 412 after multiple ablation passes. In FIG. 5 (right), region 500 represents the rendering of the target volume from pre-treatment data, such as MRI or CT data. Region 604 represents the real-time ultrasound image produced by ultrasound transducer 400, which is also represented in the display in FIG. 5 by three-dimensional rendering 602. It should be noted that in the illustrated example, pre-treatment image 500 is registered with real-time ultrasound image 604. Further, the combined image is shown from the viewpoint of the user.

Region 504 illustrated in FIG. 5 represents the portion of target volume 500 that is affected by multiple ablation passes. Wireframe mesh 700 represents the treatment volume that will be affected based on the current position of the RFA probe. Such rendering may be particularly suitable for treating large lesions to inform the interventional radiologist of portions of a large tumor that have already been ablated as well as of those that still remain to be treated.

As stated above, rendering and display module 412 may both calculate and display in real-time the amount of tumor and background tissue that would be ablated for the momentary location of the ablation probe, in order to illustrate on the display the impact of probe position. The calculation and display of the amount of tumor and background tissue that would be affected by an ablation can be performed in real-time or may use a lookup table based on the geometry and location of the probe. As stated above, the affected volume can be determined using the data from the probe manufacturer or using experimental data. The volume that would be affected by the ablation can be super imposed about the ablation probe position and displayed to the user. FIG. 7 illustrates an example of displaying the amount of tumor and background tissue that would be ablated for a particular location of the ablation probe. In FIG. 7, relative amounts of healthy and tumor tissue that would be affected by the ablation pass are shown as vertical bars in the lower left hand corner in different shading. Such a display may be useful in probe positioning to maximize the proportion of tumor tissue that is treated with respect to healthy tissue.

According to another aspect of the subject matter described herein, the guidance system will benefit from accurate registration of the user's eyes for precise head tracked stereoscopic visualization. An exemplary method for accurate registration of the user's eyes for precise head tracked stereoscopic visualization will now be described.

The high accuracy is achieved in the same calibrated, stereoscopic head-tracked viewing environment used by the guidance system. While the current implementation requires a head-mounted tracker, future embodiments may use un-encumbering tracking, such as vision-based head pose recovery. It is important to note that the technique described here does not require pupil tracking; it uses only head pose, which can generally be obtained less intrusively, with higher reliability, and from a greater distance away than camera-based pupil tracking. An additional pupil tracker is not required unless the system must know the user's gaze direction, for example in order to record user behavior in training-related applications [14].

2. Calibration System for Exact Eye Locations

The calibration system uses the following main components (FIG. 9):

a Planar Systems SD1710 ("Planar") stereoscopic display with two 17" LCD monitors and a semi-transparent mirror that reflects the upper monitor's image onto the lower monitor. The user wears linearly polarized glasses that restrict viewing of the lower monitor to the left eye and viewing of the upper monitor's reflection to the right eye. The LCDs' native resolution is 1280×1024.

a sub-millimeter precision Northern Digital Optotrak Certus optoelectronic tracking system ("Certus"). Both the Planar and the user's head are tracked by the Certus in all six degrees of freedom with clusters of infrared (IR) LEDs (11 on the head, 4 on the Planar). As mentioned, the advantage of tracking the display as in handheld augmented reality applications [15] is that both the display and the tracker can be moved with respect to each other while the system is running, for example, to improve LED visibility. The Certus also provides a calibration stylus for precise measurements (visible in FIG. 9).

The user dons the head tracker and performs a simple, fast eye calibration procedure.

2.1. Projection Origin and Eye Calibration

In fish tank VR systems, the calibration between the head tracker and the eyes is usually obtained from measurements such as the user's inter-pupillary distance (IPD, measured with a pupillometer) [8], the location of the tracker on the user's head, as well as from assumptions about the most suitable location of the projection origin inside the eye. Popular choices for the latter include the eye's 1st nodal point [2], the entrance pupil [9], and the center of the eye [10]. Our method uses the eye center [10] because it is easy to calibrate and yields exact synthetic imagery in the center of the field of view regardless of the user's gaze. However, the 1st nodal point and the entrance pupil are better approximations for the actual optics within the eye. Therefore, by rendering stereo images from the eye centers, i.e. from a few mm too far back, and thus with a slightly exaggerated separation, the EEC system deforms the stereoscopic field [11] ever so slightly. For higher accuracy, a pupil tracker could detect the user's gaze directions, and assuming that the user converges onto the virtual object found along those directions, the rendering and display module could move the projection origins forward to the 1st nodal point, or all the way to the pupil.

Calibration.

Figure 10:
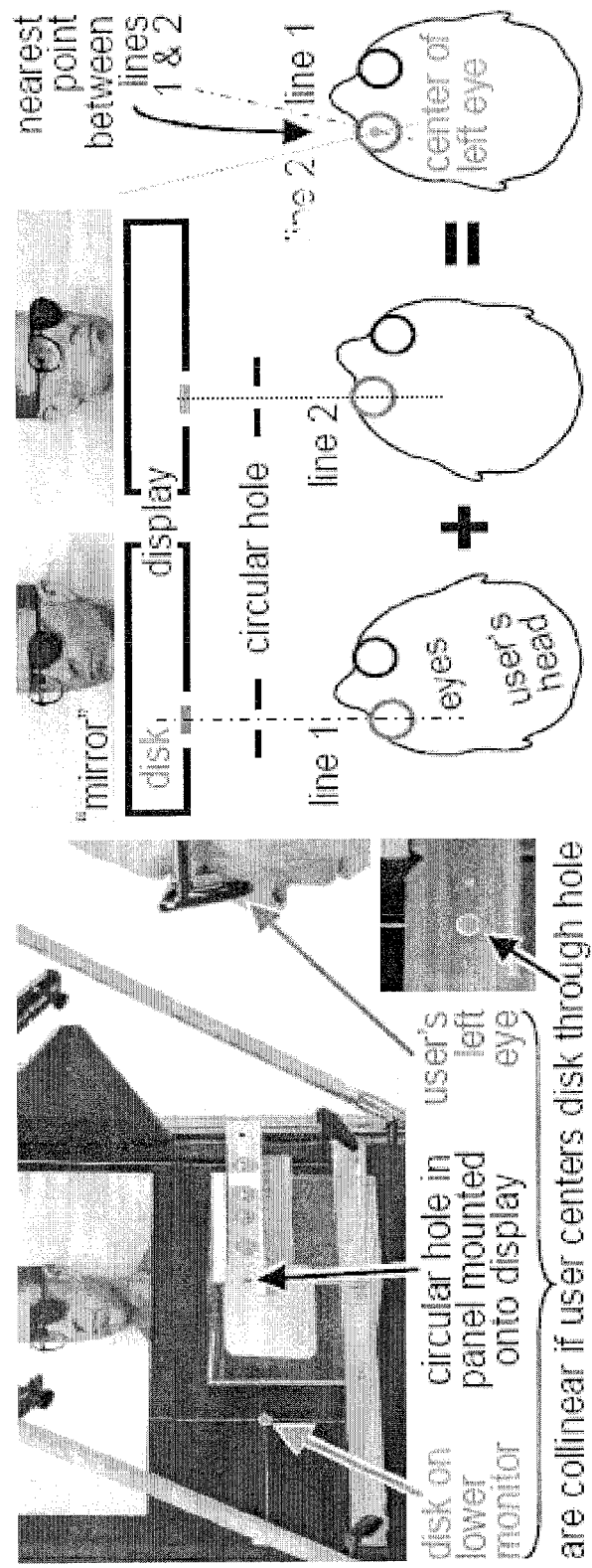
FIG. 10 illustrates an eye calibration setup and sequence, shown for the left eye only.

The eye calibration technique (FIG. 10) was inspired by previous methods [12][13] and modified for the additional display tracker. A small panel with a circular hole is temporarily mounted in front of the bottom LCD panel. Both the hole and the bottom LCD monitor are pre-calibrated (one-time only) to the Planar's tracker with the Certus calibration stylus. The eye calibration program shows a circular disk on the display. Using a "mirror image" of the user's head as a guide, the user moves and orients his head to line up the disk through the hole, twice through each eye, under different head orientations. To avoid confusion, users wear frames with one eye masked off, as shown by the "mirror" guides at the top of FIG. 10. The program collects four line equations in head tracker coordinates. In pairs of two, these four lines define the eye centers at their intersections—or rather, at the closest points between them. The entire task takes 1-2 minutes except for inexperienced first-time users, which take longer mostly because they must receive and follow instructions.

Since the current head band tracker (FIG. 9) does not guarantee repeatable positioning on the user's head, the user should not remove it between calibration and the following interactive phase (i.e., using the system to guide an ablation). User-specific head-conforming gear equipped with IR LEDs—or with passive markers for camera-based head tracking—could eliminate this restriction and could thus reduce each user's eye calibration to a one-time procedure.

Application of Eye Calibration to Image Guided Ablation

Figure 11:
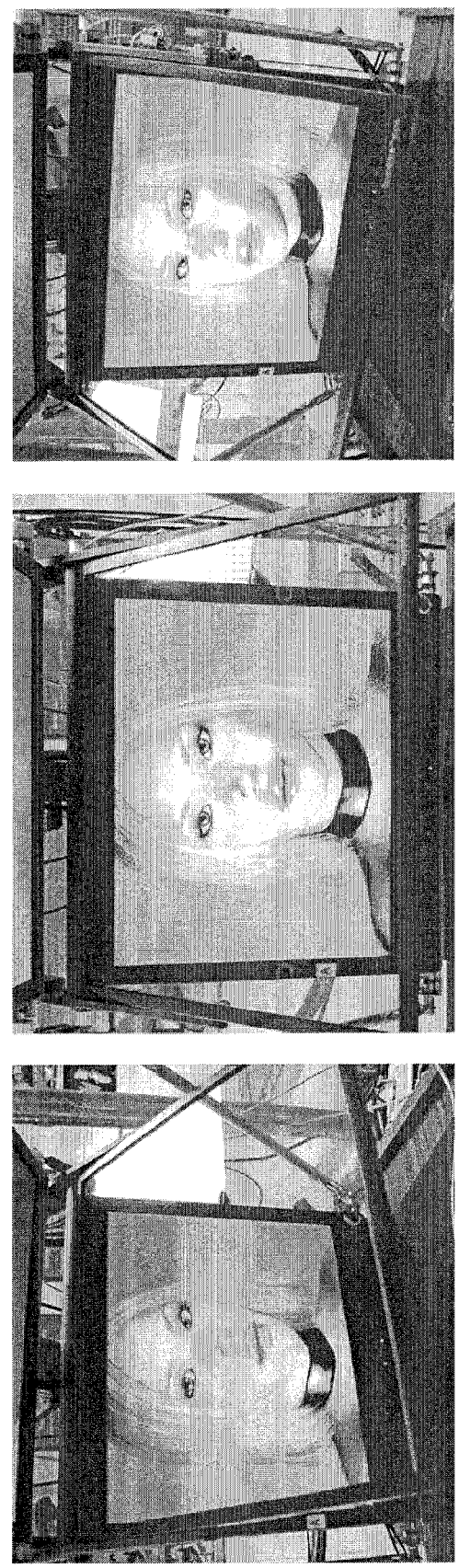
FIG. 11 is a series of images that illustrate as the user moves about the display, the virtual imagery in the display (in this case a human head for illustrative purposes) is shown from the proper perspective (i.e., from the user's eyes. The three images were photographed with the display's stereo mirror in place (cf.

As stated above, the user's head or eyes can be tracked during image guided ablation and the combined display shown by the rendering and display module 412 can adjust the combined display of the treatment volume based on the current position of the user's head and/or eyes. For example, in the images illustrated in FIG. 5, as the user is conducting an RFA procedure, the display illustrated in FIG. 5 may be continually updated based on the viewpoint of the user. As the user's head moves during treatment, the viewpoint of the display will be updated. FIG. 11 shows the stereoscopic display (in this case depicting a photorealistic human head) as seen by a head-tracked user moving around it. Note that the user is able to naturally look around the subject ("head-motion parallax") as if the display contained actual three-dimensional structures. Together with stereoscopic rendering and exact eye calibration, the illusion is almost perfect.

Exact eye calibration in an ablation procedure can be used to produce the same 3D effect illustrated in FIG. 11 in the combined image displayed by rendering and display module 412 as the user moves about display 410. For example, the exact eye calibration method described herein is used to determine whether the user's eyes are with respect to headband 406, which is tracked. When the user moves about display 410, rendering and display module 412 uses the position data from headband 406 and the offset for each eye produced during eye calibration to determine the positions of each of the user's eyes. Rendering and display module 412 produces left and right eye images based on the tracked position of headband and the eye calibration data. The left and right eye images appear as a single image on display 412 because the user wears stereoscopic glasses. An example of such a combined image viewed through stereoscopic glasses is shown in FIG. 5 (right).

Figure 12:
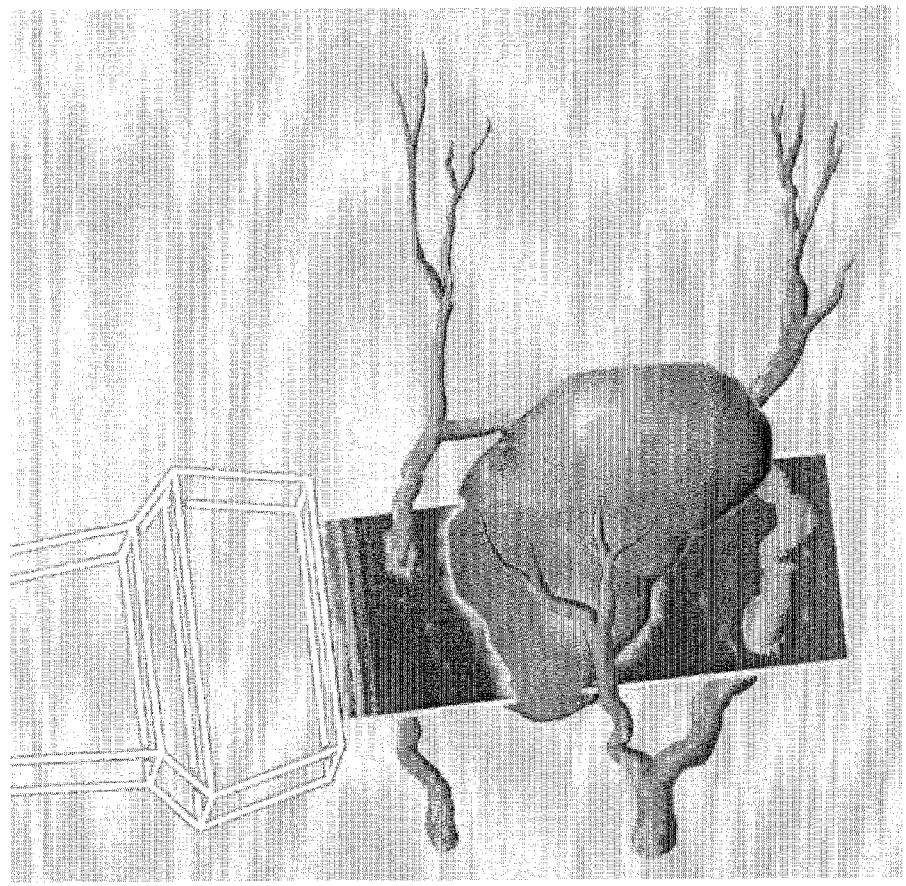
FIG. 12 is an image of an ultrasound transducer, an ultrasound image, a target volume, and an anatomical context that may be produced by a rendering and display module according to an embodiment of the subject matter described herein.

According to another aspect of the subject matter described herein, rendering and display module 412 may render preoperative data, including an anatomical context for the ablation of the target volume. For example, rendering and display module 412 may render organs or anatomical structures such as bones or blood vessels adjacent to the target volume. FIG. 12 illustrates an example of such a context.

The disclosure of each of the following references is hereby incorporated herein by reference in its entirety.

REFERENCES

[1] O. Catalano et al. "Multiphase helical CT findings after percutaneous ablation procedures for hepatocellular carcinoma." Abdom. Imaging, 25(6), 2000, pp. 607-614.

[2] Michael Deering. "High Resolution Virtual Reality." Proceedings of SIGGRAPH '92, Computer Graphics, 26 (2), 1992, pp. 195-202.

[3] G. D. Dodd et al. "Minimally invasive treatment of malignant hepatic tumors: at the threshold of a major breakthrough." Radiographics 20(1), 2000, pp. 9-27.

[4] http://www.planar.com/products/flatpanel_monitors/stereoscopic/

[5] Michael Rosenthal, Andrei State, Joohi Lee, Gentaro Hirota, Jeremy Ackerman, Kurtis Keller, Etta D. Pisano, Michael Jiroutek, Keith Muller and Henry Fuchs. "Augmented reality guidance for needle biopsies: An initial randomized, controlled trial in phantoms." Medical Image Analysis 6(3), September 2002, pp. 313-320.

[6] Andrei State, Kurtis P. Keller, Henry Fuchs. "Simulation-Based Design and Rapid Prototyping of a Parallax-Free, Orthoscopic Video See-Through Head-Mounted Display." Proc. International Symposium on Mixed & Augmented Reality 2005 (Vienna, Austria, Oct. 5-8, 2005), pp. 28-31.

[7] Andrei State. "Exact Eye Contact with Virtual Humans." Proc. IEEE International Workshop on Human Computer Interaction 2007 (Rio de Janeiro, Brazil, Oct. 20, 2007), pp. 138-145.

[8] Meehan, M., Razzaque, S., Whitton, M., Brooks, F.: Effects of Latency on Presence in Stressful Virtual Environments. Proceedings of IEEE Virtual Reality 2003, IEEE Computer Society, 141-148 (2003).

[9] Rolland, J. P., Burbeck, C. A., Gibson, W., Ariely, D.: Towards Quantifying Depth and Size Perception in 3D Virtual Environments. Presence: Teleoperators and Virtual Environments 4(1), 24-48 (1995).

[10] Holloway, R.: Registration Error Analysis for Augmented Reality. Presence: Teleoperators and Virtual Environments 6(4), 413-432 (1997).

[11] Lipton, L.: Foundations of the Stereoscopic Cinema. Van Nostrand Reinhold (1982).

[12] Azuma, R., Bishop, G.: Improving Static and Dynamic Registration in an Optical See-Through HMD. Proceedings of SIGGRAPH '94, Computer Graphics, Annual Conference Series, 1994, 197-204 (1994).

[13] Fuhrmann, A., Splechtna, R., Pikryl, J.: Comprehensive calibration and registration procedures for augmented reality. Proc. Eurographics Workshop on Virtual Environments 2001, 219-228 (2001).

[14] Raij, A. B., Johnsen, K., Dickerson, R. F., Lok, B. C., Cohen, M. S., Duerson, M., Pauly, R. R., Stevens, A. O., Wagner, P., Lind, D. S.: Comparing Interpersonal Interactions with a Virtual Human to Those with a Real Human. IEEE Transactions on Visualization and Computer Graphics 13(3), 443-457 (2007).

[15] Billinghurst, M., Henrysson, A.: Research Directions in Handheld AR. Int. J. of Virtual Reality 5(2), 51-58 (2006).

Although the examples described above relate primarily to RFA, the subject matter described herein is not limited to image guided RFA. The image guided techniques and systems described herein can be used with any type of ablation, including microwave ablation and cryo-ablation. In microwave ablation, a needle delivers microwave energy to the target volume. In cryo-ablation, a needle delivers cold fluid to the target volume. The tracking, rendering, and display techniques and systems described above can be used to track, render, and display microwave and cryo-ablation needles in the same manner described above. In addition, the techniques and systems described above for displaying predicted ablation volumes and ablated volumes for successive ablation passes can be applied to microwave and cryo-ablation probes by configuring rendering and display module 412 with manufacturer's specifications for these types of probes.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A system for image guided ablation, the system comprising:
   an ultrasound transducer configured to produce a real-time 2D ultrasound image slice of a target volume and surrounding tissue;
   an ablation probe configured to ablate the target volume;
   a display configured to display an image to guide positioning of the ablation probe during ablation of the target volume;
   at least one tracker configured to track orientations of the ablation probe, the ultrasound transducer, and a user's head during the ablation of the target volume, wherein the at least one tracker is distinct from the display; and
   a rendering and display module configured to:
      receive a 3D pre-ablation-treatment image of the target volume;
      receive the real-time 2D ultrasound image slice from the ultrasound transducer;
      receive data regarding the tracked orientation of the ablation probe, the ultrasound transducer, and the user's head produced by the at least one tracker;
      determine a perspective view of the 3D pre-ablation-treatment image in a virtual 3D space based at least in part on the tracked orientation of the user's head;
      determine a perspective view of the real-time 2D ultrasound image slice in the virtual 3D space based at least in part on the tracked orientations of the ultrasound transducer and the user's head;
      determine a perspective view of a virtual 3D ablation probe in the virtual 3D space based at least in part on the tracked orientations of the ablation probe and the user's head, wherein the virtual 3D ablation probe corresponds to the ablation probe;
      determine a perspective view of a virtual 3D ultrasound transducer in the virtual 3D space based at least in part on the tracked orientations of the ultrasound transducer and the user's head, wherein the virtual 3D ultrasound transducer corresponds to the ultrasound transducer;
      cause the display to simultaneously and continuously display the perspective view of the 3D pre-ablation-treatment image, the perspective view of the real-time 2D ultrasound image slice, the perspective view of the virtual 3D ablation probe, and the perspective view of the virtual 3D ultrasound transducer in the virtual 3D space based at least in part on a location of the ultrasound transducer and the ablation probe;
      subtract from the perspective view of the 3D pre-ablation-treatment image a volume affected by a pass of the ablation probe over a portion of the target volume, wherein the volume affected by the pass of the ablation probe over the portion of the target volume is determined based on a tracked position of the ablation probe at a time of the pass of the ablation probe over the portion of the target volume, a geometry of the ablation probe, and a power setting of the ablation probe at the time of the pass of the ablation probe over the portion of the target volume; and
      cause the display to display, for a momentary position of the probe, relative amounts of healthy and tumor tissue that would be affected by an ablation pass.

2. The system of claim 1, wherein the ablation probe comprises at least one of: a radio frequency ablation (RFA) probe, a microwave ablation probe, or a cryo-ablation probe.

3. The system of claim 1, wherein the rendering and display module is further configured to:
receive eye calibration data indicating positions of the user's left and right eyes with respect to a tracked position and the tracked orientation of the user's head; and
cause the display to display a stereoscopic image with left and right eye images generated based at least in part on the eye calibration data and the tracked position and orientation of the user's head.

4. The system of claim 1, wherein the perspective view of the virtual 3D ablation probe in the virtual 3D space maintains a parallel orientation with respect to the ablation probe at least during the ablation of the target volume.

5. The system of claim 1, wherein the rendering and display module is further configured to render pre-operative data including an anatomical context for the ablation of the target volume.

6. The system of claim 1, wherein the rendering and display module is further configured to render and cause the display to display a volume that will be affected by an ablation pass for a current position and orientation of the ablation probe and for its operational specifications.

7. The system of claim 1, wherein the rendering and display module is further configured to render guidance graphics including schematic 3D structures to emphasize a spatial relationship of the real-time 2D ultrasound image slice and the ablation probe.

8. The system of claim 1, wherein the rendering and display module is further configured to cause the display to display the perspective view of the real-time 2D ultrasound image slice and the perspective view of the virtual 3D ablation probe in one of:
a centered mode in which the real-time 2D ultrasound image slice is always shown in the center of the display, wherein it is not possible to move the ultrasound transducer such that the perspective view of the virtual 3D ultrasound transducer is not displayed on the display; and
a free mode in which the user can interactively define a position offset between an area within a patient and the virtual 3D space of the display, wherein translational motion of the ablation probe and the ultrasound transducer results in translational motion of the perspective view of the virtual 3D ablation probe and the perspective view of the virtual 3D ultrasound transducer in the virtual 3D space, and wherein it is possible to move the ultrasound transducer such that the perspective view of the virtual 3D ultrasound transducer is not displayed on the display.

9. The system of claim 1, further comprising a tine deployment tracker configured to track deployment of tines of the ablation probe and to provide tine deployment tracking data to the rendering and display module, wherein the rendering and display module is further configured to cause the display to display ablation probe tine deployment.

10. A method for producing an image suitable for image guided ablation, the method comprising:
receiving a real-time 2D ultrasound image slice of a target volume and surrounding tissue from an ultrasound transducer;
receiving a 3D pre-ablation image of the target volume;
tracking, using at least one tracker, orientations of an ablation probe, the ultrasound transducer, and a user's head during ablation of the target volume;
determining a perspective view of the 3D pre-ablation-treatment image in a virtual 3D space based at least in part on the tracked orientation of the user's head;
determining a perspective view of the real-time 2D ultrasound image slice in the virtual 3D space based at least in part on the tracked orientations of the ultrasound transducer and the user's head;
determining a perspective view of a virtual 3D ablation probe in the virtual 3D space based at least in part on the tracked orientations of the ablation probe and the user's head, wherein the virtual 3D ablation probe corresponds to the ablation probe;
determining a perspective view of a virtual 3D ultrasound transducer in the virtual 3D space based at least in part on the tracked orientations of the ultrasound transducer and the user's head, wherein the virtual 3D ultrasound transducer corresponds to the ultrasound transducer;
causing a display to simultaneously and continuously display the perspective view of the 3D pre-ablation-treatment image, the perspective view of the real-time 2D ultrasound image slice, the perspective view of the virtual 3D ablation probe, and the perspective view of the virtual 3D ultrasound transducer in the virtual 3D space based at least in part on a location of the ultrasound transducer and the ablation probe, wherein the display is distinct from the at least one tracker;
subtracting from the perspective view of the 3D pre-ablation image a volume affected by a pass of the ablation probe over a portion of the target volume, wherein the volume affected by the pass of the ablation probe over the portion of the target volume is determined based on a tracked position of the ablation probe at a time of the pass of the ablation probe over the portion of the target volume, a geometry of the ablation probe, and a power setting of the ablation probe at the time of the pass of the ablation probe over the portion of the target volume; and
causing the display to display, for a momentary position of the probe, relative amounts of healthy and tumor tissue that would be affected by an ablation pass.

11. The method of claim 10, wherein the ablation probe comprises one of: a radio frequency ablation (RFA) probe, a microwave ablation probe, and a cryoablation probe.

12. The method of claim 10, further comprising:
receiving eye calibration data regarding positions of a user's left and right eyes; and
causing the display to display a stereoscopic image including left and right eye images generated based at least in part the eye calibration data and a tracked position and the tracked orientation of the user's head.

13. The method of claim 10, wherein the perspective view of the virtual 3D ultrasound transducer and the perspective view of the virtual 3D ablation probe maintain a parallel orientation with respect to the ultrasound transducer and the ablation probe, respectively, at least during guidance of the ablation probe to the target volume and during the ablation of the target volume.

14. The method of claim 10, further comprising rendering preoperative data including an anatomical context for the ablation of the target volume.

15. The method of claim 10, further comprising rendering and causing the display to display a predicted treatment volume for a current position and orientation of the ablation probe and for its operational specifications.

16. The method of claim 10, further comprising rendering guidance graphics including schematic 3D structures to emphasize a spatial relationship between the real-time 2D ultrasound image slice and the ablation probe.

17. The method of claim 10, further comprising causing the display to display the perspective view of the real-time 2D ultrasound image slice and the perspective view of the virtual 3D ablation probe in one of the following modes:
- a centered mode in which the real-time 2D ultrasound image slice is always shown in the center of the display, wherein it is not possible to move the ultrasound transducer such that the perspective view of the virtual 3D ultrasound transducer is not displayed on the display;
- a free mode in which the user can interactively define a position offset between an area within a patient and the virtual 3D space of the display, wherein translational motion of the ablation probe and the ultrasound transducer results in translational motion of the perspective view of the virtual 3D ablation probe and the perspective view of the virtual 3D ultrasound transducer in the virtual 3D space, and wherein it is possible to move the ultrasound transducer such that the perspective view of the virtual 3D ultrasound transducer is not displayed on the display.

18. The method of claim 10, further comprising:
tracking deployment of tines of the ablation probe; and
causing the display to display a position of the tines of the ablation probe in the virtual 3D space.

19. A non-transitory computer readable medium having stored thereon executable instructions that when executed by a processor of a computer perform steps, the steps comprising:
- receiving a real-time 2D ultrasound image slice of a target volume and surrounding tissue from an ultrasound transducer;
- receiving a 3D pre-ablation image of the target volume;
- tracking, using at least one tracker, orientations of an ablation probe, the ultrasound transducer, and a user's head during ablation of the target volume;
- determining a perspective view of the 3D pre-ablation-treatment image in a virtual 3D space based at least in part on the tracked orientation of the user's head;
- determining a perspective view of the real-time 2D ultrasound image slice in the virtual 3D space based at least in part on the tracked orientations of the ultrasound transducer and the user's head;
- determining a perspective view of a virtual 3D ablation probe in the virtual 3D space based at least in part on the tracked orientations of the ablation probe and the user's head, wherein the virtual 3D ablation probe corresponds to the ablation probe;
- determining a perspective view of a virtual 3D ultrasound transducer in the virtual 3D space based at least in part on the tracked orientations of the ultrasound transducer and the user's head, wherein the virtual 3D ultrasound transducer corresponds to the ultrasound transducer;
- causing a display to simultaneously and continuously display the perspective view of the 3D pre-ablation-treatment image, the perspective view of the real-time 2D ultrasound image slice, the perspective view of the virtual 3D ablation probe, and the perspective view of the virtual 3D ultrasound transducer in the virtual 3D space based at least in part on a location of the ultrasound transducer and the ablation probe;
- subtracting from the perspective view of the 3D pre-ablation image a volume affected by a pass of the ablation probe over a portion of the target volume, wherein the volume affected by the pass of the ablation probe over the portion of the target volume is determined based on a tracked position of the ablation probe at a time of the pass of the ablation probe over the portion of the target volume, a geometry of the ablation probe, and a power setting of the ablation probe at the time of the pass of the ablation probe over the portion of the target volume; and
- causing the display to display, for a momentary position of the probe, relative amounts of healthy and tumor tissue that would be affected by an ablation pass.

20. The system of claim 1, wherein the perspective view of the real-time 2D ultrasound image slice and the perspective view of the virtual 3D ultrasound transducer are displayed in the virtual 3D space when the ultrasound transducer is located within a predetermined area and the perspective view of the real-time 2D ultrasound image slice and the perspective view of the virtual 3D ultrasound transducer are not displayed in the virtual 3D space when the ultrasound transducer is located outside the predetermined area.

21. The system of claim 1, wherein the perspective view of the virtual 3D ablation probe is displayed in the virtual 3D space when the ablation probe is located within a predetermined area and the perspective view of the virtual 3D ablation probe is not displayed in the virtual 3D space when the ablation probe is located outside the predetermined area.

* * * * *